US008802656B2

(12) United States Patent
Lichtenberger

(10) Patent No.: US 8,802,656 B2
(45) Date of Patent: Aug. 12, 2014

(54) PURIFIED PHOSPHOLIPID-NON-STEROIDAL ANTI-INFLAMMATORY DRUG ASSOCIATED COMPOSITIONS AND METHODS FOR PREPARING AND USING SAME

(75) Inventor: Lenard Lichtenberger, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 234 days.

(21) Appl. No.: 11/249,051

(22) Filed: Oct. 12, 2005

(65) Prior Publication Data

US 2006/0078574 A1 Apr. 13, 2006

Related U.S. Application Data

(60) Provisional application No. 60/617,732, filed on Oct. 12, 2004, provisional application No. 60/682,440, filed on May 19, 2005.

(51) Int. Cl.
*A61K 31/683* (2006.01)
*A61K 31/685* (2006.01)
*A61K 31/688* (2006.01)
*A61K 31/60* (2006.01)
*A61K 31/616* (2006.01)

(52) U.S. Cl.
CPC ............. *A61K 31/683* (2013.01); *A61K 31/685* (2013.01); *A61K 31/688* (2013.01); *A61K 31/60* (2013.01); *A61K 31/616* (2013.01)
USPC .............. 514/78; 514/114; 514/570; 514/165

(58) Field of Classification Search
CPC . A61K 31/683; A61K 31/685; A61K 31/688; A61K 31/60; A61K 31/616
USPC .................................. 514/78, 114, 570, 165
See application file for complete search history.

(56) References Cited

U.S. PATENT DOCUMENTS 5,763,422 A * 6/1998 Lichtenberger et al. ........ 514/78

FOREIGN PATENT DOCUMENTS

| EP | 0 161 445 A1 | 11/1985 |
|---|---|---|
| WO | WO 00/30444 | 6/2000 |
| WO | WO 02/085414 A2 | 10/2002 |

OTHER PUBLICATIONS

PCT Notification of Transmittal of the International Search Report and the Written Opinion of the International Searching Authority, or the Declaration dated Jul. 7, 2006.
Kurinets, Alexander, et al., Phosphatidylcholine-Associated Aspirin Accelerates Healing of Gastric Ulcers in Rats, Digestive Diseases and Sciences, Apr. 1998, pp. 786-790, vol. 43 No. 4.
European Patent Office, Response to Official Action, Serial No. 05817073.9, Feb. 15, 2010.
Chinese Patent Office, Official Action, Serial No. 200580040620.7, Mar. 18, 2010.
Australian Patent Office, Official Action, Serial No. 2005295874, Apr. 13, 2010.
Chinese Patent Office, Response to the Second Office Action and Amended Claims, Application No. 2005800406207, Aug. 2, 2010.
Chinese Patent Office, Official Action, Serial No. 200580040620.7, Nov. 10, 2010.
Australian Patent Office, Response to Examiner's Report, Serial No. 2005295874, Dec. 14, 2010.
Chinese Patent Office, Office Action (Rejection Decision, in Chinese), Application No. 200580040620.7, Dec. 2, 2011.
Chinese Patent Office, Office Action (Rejection Decision, in English), Application No. 200580040620.7, Dec. 2, 2011.
Indian Patent Office; Response to First Examination Report; Application No. 1504/KOLNP/2007, Dec. 26, 2011.
Japanese Patent Office, Amendment, Application No. 2007-536803, Apr. 24, 2012.
Japanese Patent Office, Amendment (English translation), Application No. 2007-536803, Apr. 24, 2012.
Japanese Patent Office, Argument, Application No. 2007-536803, Apr. 24, 2012.
Japanese Patent Office, Argument (English translation), Application No. 2007-536803, Apr. 24, 2012.
Israel Patent Office; Response to Office Action filed May 23, 2010; Israeli Patent Application No. 182505.
Israel Patent Office; Office Action dated Aug. 24, 2010; Israeli Patent Application No. 182505.
Mexico Patent Office; Office Action dated Oct. 13, 2010; Mexican Patent Application No. MX/a/2007/004376.
India Patent Office; Office Action dated Jan. 20, 2011; Indian Patent Application No. 1504/KOLNP/2007.
Chinese Patent Office, Response to Office Action, Serial No. 200580040620.7, Mar. 25, 2011.
Israel Patent Office, Response to Official Action, Application No. 182505, Apr. 26, 2011.
Israel Patent Office, Response to Office Action, Application No. 182505, Jul. 8, 2012, 16 pages.
Japanese Patent Office, Office Action (Final Rejection), Application No. 2007-536803, Jul. 17, 2012, 5 pages.
Canada Patent Office, Office Action, Application No. 2,584,505, May 22, 2012, 3 pages.
Canada Patent Office, Response to Office Action, Application No. 2,584,505, Nov. 22, 2012, 31 pages.
Chinese Patent Office, Response to Office Action (in Chinese), Application No. 200580040620.7, Jun. 17, 2013, 13 pages.
Chinese Patent Office, Response to Office Action (in English), Application No. 200580040620.7, Jun. 17, 2013, 11 pages.
Japanese Patent Office, Office Action, Application No. 2007-536803, Oct. 14, 2011.
Japanese Patent Office, Office Action (English translation), Application No. 2007-536803, Oct. 14, 2011.

(Continued)

*Primary Examiner* — Bong-Sook Baek
(74) *Attorney, Agent, or Firm* — Jackson Walker L.L.P.

(57) ABSTRACT

A new pharmaceutical composition is disclosed comprising a purified phospholipid-selective and/for nonselective non-steroidal, anti-inflammatory drug associated complex and methods for making and using same. A screening method for identifying compounds that form phospholipid associated complexes is also disclosed.

4 Claims, 12 Drawing Sheets

(56) References Cited

OTHER PUBLICATIONS

Chinese Patent Office, Office Action (in Chinese), Application No. 200580040620.7, Mar. 1, 2013, 13 pages.
Chinese Patent Office, Office Action (in English), Application No. 200580040620.7, Mar. 1, 2013, 13 pages.
Israel Patent Office, Response to Office Action, Application No. 182505, Dec. 4, 2011, 6 pages.
Israel Patent Office, Office Action, Application No. 182505, Feb. 9, 2012, 2 pages.
Chinese Patent Office, Response to Request for Reexamination, Application No. 200580040620.7, Mar. 19, 2012, 5 pages.
Korean Patent Office, Office Action (Notice of Preliminary Rejection), Application No. 10-2007-7010668, Aug. 16, 2012, 7 pages.
Korean Patent Office, Office Action (Notice of Preliminary Rejection)—English translation, Application No. 10-2007-7010668, Aug. 16, 2012, 8 pages.
Israel Patent Office, Notification of Defects of Patent Application, Application No. 182505, Jul. 3, 2011.
Lichtenberger, Lenard M.; et al, Phosphatidylcholine Association Increases the Anti-Inflammatory and Analgesic Activity of Ibuprofen in Acute and Chronic Rodent Models of Joint Inflammation: Relationship to Alterations in Bioavailability and Cyclooxygenasa-inhibitory Potency; The Journal of Pharmacology and Experimental Therapeutics, vol. 298, No. 1, pp. 279-287, Mar. 22, 2001.
Mexico Patent Office, Office Action, Application No. MX/a/2007/004376, Oct. 13, 2010.
Mexico Patent Office, Response to Office Action, Application No. MX/a/2007/004376, Feb. 22, 2011.
Mexico Patent Office, Office Action, Application No. MX/a/2007/004376, Apr. 12, 2011.
Canada Patent Office, Office Action, Application No. 2,584,505, Mar. 18, 2013, 4 pages.
Israel Patent Office, Office Action, Application No. 182505, Feb. 21, 2013, 1 page.

\* cited by examiner

PURIFIED PHOSPHOLIPID-NON-STEROIDAL ANTI-INFLAMMATORY DRUG ASSOCIATED COMPOSITIONS AND METHODS FOR PREPARING AND USING SAME

RELATED APPLICATIONS

This application claims provisional priority to U.S. Provisional Patent Application Ser. Nos. 60/617,732, filed 12 Oct. 2004 and 60/682,440, filed 19 May 2005.

GOVERNMENTAL INTEREST

This invention was made with government support under Grant No. R42 DK063882 awarded by the National Institutes of Health. The government has certain rights in the invention.

BACKGROUND OF THE INVENTION

1. Field of Invention

The present invention relates to high purity associated complexes of a phospholipid (PL) and a selective and/or nonselective non-steroidal, anti-inflammatory drug (sns-NSAID) and to methods for making and using same. The present invention also relates to method for screening compounds including pharmaceutical agents (PA) for either ability to increase the solubility of a phospholipid (PL) in a solvent in which the PL has a moderate solubility, has a low solubility or is insoluble.

More particularly, the present invention relates to high purity associated complexes of a phospholipid (PL) and a selective and/or nonselective non-steroidal, anti-inflammatory drug and to methods for making and using same, where the complexes comprise polar solvent soluble, PL-sns-NSAID complexes. The method includes the steps of adding a selective and/or nonselective non-steroidal, anti-inflammatory drug (sns-NSAID) and a phospholipid (PL) to a polar solvent and then removing the polar solvent with or without cooling in the presence or absence of a vacuum to form the purified PL-sns-NSAID associated complexes. The present invention also relates to method for screening pharmaceutical agents (PAs) including adding the PA to a solvent in which the PL has a moderate solubility, has a low solubility or is insoluble and then adding a PL to determine whether the solubility of the PL is increased.

2. Description of Related Art

Phospholipids are known to associate with pharmaceutical agents such as selective and nonselective nonsteroidal anti-inflammatory drugs (sns-NSAIDs which include NSAIDs and/or COX-2 inhibitors) that are well known to be associated with gastrointestinal (GI), hepatic and renal adverse side effects, with gastroduodenal ulceration and bleeding being most common and tend to reduce if not eliminate these adverse health risks.

The following Foreign Patents, United States Patents and United States Pending Patent Applications set the prior art relevant to this application: GB 0092121, U.S. Pat. No. 4,332, 795; U.S. Pat. No. 4,369,182; U.S. Pat. No. 4,378,354; U.S. Pat. No. 4,421,747; U.S. Pat. No. 4,528,193; U.S. Pat. No. 4,687,766; U.S. Pat. No. 4,748,157; U.S. Pat. No. 4,918,063; U.S. Pat. No. 4,950,656; U.S. Pat. No. 5,032,585; U.S. Pat. No. 5,043,329; U.S. Pat. No. 5,763,422; U.S. Pat. No. 5,955, 451; U.S. Ser. No. 10/433,454; U.S. Ser. No. 10/909,748, and U.S. Ser. No. 10/909,751, incorporated herein by reference. These references demonstrated that phospholipids can reduce or eliminate the GI toxicity of the NSAIDs.

Although phospholipids are known to reduce the GI toxicity of NSAIDs and to form associated complexes, there is a need in the art for high purity PL-sns-NSAID associated complexes, for method for making and using same. There is also a need in the art for methods for screening pharmaceutical agents that can form associated complexes with phospholipids.

SUMMARY OF INVENTION

Methods for Preparing High Purity PL-NSAID Associated Compositions

The present invention provides a method including the step of contacting one selective and/or nonselective nonsteroidal anti-inflammatory drug (sns-NSAID) or a plurality of sns-NSAIDs and one phospholipid (PL) or a plurality of PLs in a polar solvent under conditions adapted to produce purified PL-sns-NSAID associated complexes, where the purified PL-sns-NSAID associated complexes include an amount of PL in excess of an amount of PL soluble in the solvent in the absence of the sns-NSAID. In one embodiment, the amount of excess PL is below an amount, based on the amount of sns-NSAID, where the PL begins to precipitate out of solution. Once the desired ratio of PL to sns-NSAID is achieved, the solvent is removed by any standard solvent removal process including evaporation, freeze drying, vacuum distillation, vacuum assisted evaporation, force gas evaporation, rotary evaporation or any similar solvent stripping or removal process.

Purified PL-NSAID Compositions

The present invention provides a composition comprising a purified PL-sns-NSAID associated complex, where the purified PL-sns-NSAID associated complex includes an amount of the PL greater than an amount of the PL soluble in a polar organic solvent in the absence of the sns-NSAID, where the PL has moderate, low or no solubility in the polar solvent.

The present invention also provides a medicament including a purified PL-sns-NSAID associated complex of this invention, where the medicament is in the form of a soft or hard capsule, a tablet, a tablet having a water-impermeable coating, a dispersion in a bio-compatible oil, a dispersion in an aqueous solution.

Method for Administering a Medicament

The present invention also provides a method for administering a medicament to an animal including a human including the step of administering to the animal an effective amount of a medicament, where the medicament is prepared by contacting one selective and/or nonselective nonsteroidal anti-inflammatory drug (sns-NSAID) or a plurality of sns-NSAIDs and one phospholipid (PL) or a plurality of PLs in a polar solvent under conditions adapted to produce purified PL-sns-NSAID associated complexes, where the purified PL-sns-NSAID associated complexes include an amount of PL in excess of an amount of PL normally soluble in the solvent in the absence of the NSAID. In one embodiment, the amount of excess PL is below an amount, based on the amount of sns-NSAID, where the PL begins to precipitate out of solution. Once the desired ratio of PL to sns-NSAID is achieved, the solvent is removed by any standard solvent removal process including evaporation, freeze drying, vacuum distillation, vacuum assisted evaporation, force gas evaporation, rotary evaporation or any similar solvent stripping or removal process.

Methods for Screening Compounds

The present invention also provides a method for screening compounds for their ability to solubilize a phospholipid (PL) in a solvent in which the phospholipid has moderate solubility, low solubility or no solubility. The inventor believes that compounds that increase the solubility of the PL in such solvents are compounds that form associated complexes with the PL. The method includes the step of adding an amount of a PL to a solvent, in which the PL has moderate solubility, low solubility or no solubility, to form a PL-solvent mixture, where the amount of PL is above the PL solubility in the solvent such that a precipitate is present. Once the PL-solvent mixture is formed, a test compound is added to the PL-solvent mixture with stirring and with or without heating. If some or all of the precipitate dissolves, then determining an amount of the compound needed to substantially completely eliminate the precipitate or the amount of PL that can be pulled into solution with the test compound. If a solution is formed having no precipitates, then the solvent is removed to form a composition of the PL and the compound. The inventor believes that compounds capable of solubilizing PL in such a solvent are those capable of forming association complexes with the PL and the resulting compositions represent purified PL-compound complexes.

The present invention provides to an alternate method for screening compounds for their ability of solubilize a PL in a solvent in which the phospholipid has moderate solubility, low solubility or no solubility. The method includes the step of dissolving a compound-to-be-screened in a solvent in which the phospholipid has moderate solubility, low solubility or no solubility. After preparing the compound solution, an amount of the PL in excess of its solubility in the solvent is added with stirring and with or without heating. If no precipitate forms or if a precipitate forms and then goes away, then determining an amount of the PL needed to result in the formation of a persistent precipitate. If a solution is formed having no precipitates, then the solvent can be removed to form a composition of the PL and the compound that is soluble in the solvent and is believed to represent a purified PL-compound associated complex. In one embodiment, the screening method is directed to screening pharmaceutically active agents (PAs) to form compositions including PL-PA associated complexes. New PL-PA compositions may benefit from the presence of PL in the associated complex, such benefits can include decreased GI toxicity, increased compound bio-availability, increased membrane permeability, and increased therapeutic activity of the PA or other similar benefits known to be associated with phospholipids. In another embodiment, the method is used to find chemicals that form such PL complexes for use in other industrial and research areas.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
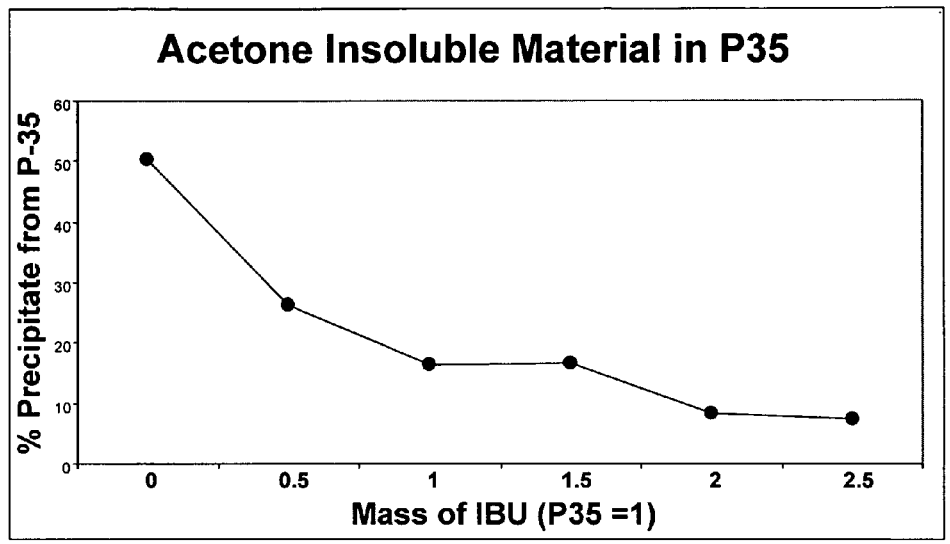
FIG. 1 depicts a plot of acetone precipitables versus weight of added ibuprofen using P35SB as the source of PC.

The inventor has found that enriched and/or purified composition including one phospholipid (PL) or a plurality of phospholipids (PLs) and one selective and/or nonselective non-steroidal, anti-inflammatory drug (sns-NSAID which include NSAIDs and COX-2 inhibitors) or a plurality of sns-NSAIDs can be prepared, where the complexes are characterized in that the NSAID increases a solubility of the PL in a polar solvent in which the PL has moderate, low or no solubility. Once the solvent is removed, the PL-sns-NSAID compositions represent compositions that include substantially pure PL-NSAID associated complexes. The inventor has found that such high purity PL-sns-NSAID compositions have enhanced gastrointestinal (GI) safety or reduced GI toxicity as compared to the sns-NSAID alone. The inventor has also found that purified PL-NSAID compositions have similar and often superior GI safety properties than PL-NSAID compositions not formed in the above polar solvent process, which of course have superior GI safety and enhanced efficacy to the NSAID alone. These purified PL-NSAID compositions also show similar and often superior NSAID efficacies in in vivo animal trials and PL-NSAID composition made by conventional methods. Unless otherwise specified and ratios are weight percent (wt. %) ratios and all formulation are expressed in weight percent (wt. %). Although various analytical evidence is now being developed to determine the exact nature and structure of the association complexes formed between Pls and selective and nonselective non-steroidal, anti-inflammatory drug (e.g., traditional NSAIDs and COX-2 inhibitors), the exact nature and structure of such complexes is still a matter of discussion. Thus, the term associated complex or associated complexes is designed to mean any chemical and/or physical association between a PL and an sns-NSAID or any other compound that increases the solubility of the PL in a polar solvent such as acetone.

The novel methods and compositions derived therefrom of this invention are based on observations by the inventor that PLs have limited solubility in certain polar organic solvents and that NSAIDs substantially increase the solubility of the PL in such solvents. The inventor believes that this increased PL solubility is caused by the formation of association complexes between the PL and the NSAID. In fact, the NSAID can increase the amount of PL soluble in the solvent from several grams per 15 mL of solvent (<2 grams/15 mL) to >50 grams/15 mL of solvent. Moreover, the inventor believes and analytical data confirms that the resulting compositions, once the solvent is removed represent purified PL-NSAID associated complexes allowing NSAID compositions to be prepared based on these purified PL-NSAID associated complexes. Such NSAID compositions can then be administered to an animal including an human orally, enterally, rectally, topically, intravenously, intra-arterially, or directly in a tissue site to ameliorate inflammation, pain, fever, thrombosis or other symptoms and/or conditions (e.g., cancer, heart disease, Alzheimer's Disease) for which the NSAIDs are known to be of therapeutic value.

Moreover, purified PL-NSAID associated complexes prepared in accordance with the methods of this invention and compositions made therefrom generally have been shown to have superior gastrointestinal (GI) safety and enhanced therapeutic efficacy over the NSAID alone or PL-NSAID composition prepared by conventional methods. The inventor believes that the method of the present invention will allow the preparation of other purified phospholipid-pharmaceutical agent (PL-PA) associated complexes that will benefit from PL.

The composition of this invention can be used alone or combined with compositions set forth in the following Foreign Patents, United States Patents and United States Pending Patent Applications set the prior art relevant to this application: GB 0092121, U.S. Pat. No. 4,332,795; U.S. Pat. No. 4,369,182; U.S. Pat. No. 4,378,354; U.S. Pat. No. 4,421,747; U.S. Pat. No. 4,528,193; U.S. Pat. No. 4,687,766; U.S. Pat. No. 4,748,157; U.S. Pat. No. 4,918,063; U.S. Pat. No. 4,950,656; U.S. Pat. No. 5,032,585; U.S. Pat. No. 5,043,329; U.S. Pat. No. 5,763,422; U.S. Pat. No. 5,955,451; U.S. Ser. No. 10/433,454; U.S. Ser. No. 10/909,748, and U.S. Ser. No. 10/909,751, incorporated herein by reference.

The composition of the present invention can be used for treating any medical condition for which the sns-NSAID and the PL are known now or later becomes known to be efficacious. Thus, the compositions can be used to reduce or inhibit pain, inflammation, fever, platelet aggregation, etc. and/or to treat or prevent diseases for which the sns-NSAID is known now or later to be efficacious such as arthritis (rheumatoid and osteoarthritis) other chronic inflammatory diseases, stroke, traumatic brain injury, spinal chord injury, peripheral neuropathy, other neurological disorders, Alzheimer's disease, thrombosis, myocardial infarction, other cardiovascular diseases, certain varieties of cancer including, without limitation, colon, breast, ovarian, prostate, bladder, leukemia, pancreatic, esophageal or other similar cancers.

The present invention broadly relates to a method for producing purified PL-sns-NSAID associated complexes. The method generally includes the step of contacting one sns-NSAID or a plurality of sns-NSAIDs and one PL or a plurality of PLs in a polar solvent under conditions adapted to produce the purified PL-sns-NSAID associated complexes, where the purified PL-sns-NSAID associated composition provides enhanced GI safety and similar or enhanced therapeutic efficacy and/or effectiveness compared either to the sns-NSAID alone or to a conventionally prepared PL-sns-NSAID compositions.

The present invention also broadly relates to a composition comprising purified PL-sns-NSAID associated complexes, where the purified PL-sns-NSAID associated complexes generally have superior GI safety and improved efficacy compared to the sns-NSAID alone or a conventionally prepared PL-sns-NSAID composition. The purified PL-sns-NSAID associated complexes are soluble in a polar solvent at a given temperature, where the amount of PL exceed the amount of PL that is soluble in the solvent under these conditions in the absence of the sns-NSAID.

Methods for Preparing Purified PL-Associated Complexes

In one embodiment of the present invention, a method is disclosed including the step of contacting one NSAID or a plurality of NSAIDs and one PL or a plurality of PLs in a polar solvent under conditions adapted to produce purified PL-NSAID associated complexes. After solvent removal, the purified PL-NSAID associated complexes or compositions made therefrom provide similar and often enhanced GI safety compared to conventionally prepared PL-NSAID associated complexes and superior GI safety compared to the NSAID alone.

In another embodiment of the present invention, a method is disclosed including the step of contacting one NSAID or a plurality of NSAIDs and one phosphatidylcholines (PC) or a plurality of PCs in a polar solvent under conditions adapted to produce purified PC-NSAID associated complexes after solvent removal.

In another embodiment of the present invention, a method is disclosed including the step of adding an amount of an NSAID and an amount of a PL to a polar solvent for a dissolution time and at a dissolution temperature sufficient to completely dissolve the NSAID and the PL. Once the NSAID and the PL are dissolved, the solution is cooled for a cooling time and to a cooling temperature sufficient to precipitate any PL in excess of an association amount of the PL based on the amount of NSAID initially added. The association amount is a maximum amount of the PL that associates with the amount of NSAID under the given conditions, i.e., upon cooling, no PL precipitate is formed. Of course, the maximum amount of PL varies for each PL-NSAID combination and for each solvent used. Any precipitate formed upon cooling is removed by filtration, centrifugation, or the like. After precipitate removal, the solvent is removed below a desired level, an FDA required level or below a detection limit for the solvent to produce a purified PL-NSAID associated complex.

In another embodiment of the present invention, a method is disclosed including the step of adding a NSAID and a PC to a polar solvent for a dissolution time and at a dissolution temperature, where the dissolution time and dissolution temperature are sufficient to completely dissolve the NSAID and PC. After dissolution with little or no precipitate, the solvent is removed by a solvent removal step for a removal time and at a removal temperature sufficient to remove the solvent below a desired low level, an FDA required level or below a detection limit for the solvent to produce a purified PC-NSAID associated complex or composition.

In another embodiment of the present invention, a method is disclosed including the step of combining an NSAID or a plurality of NSAIDs and an PL or a plurality of PLs in a polar solvent for a time and at a temperature sufficient to completely dissolve the NSAIDs and the PLs to form a PL-NSAID solution. The PL-NSAID solution is then rapidly cooled to a precipitation temperature sufficient to allow any excess PL to precipitate out of solution. The sudden drop in temperature allows free PL to precipitate out of solution forming an enriched or purified PL-NSAID associated composition. The solvent is then removed by evaporation under an inert atmosphere in the absence or presence of a vacuum and/or in the presence or absence of heating to recover the enriched or purified PL-NSAID associated composition. Alternatively, the solvent can be removed by lyophilization, freeze-drying or other similar solvent removal process. Once a particular ratio of PL to NSAID has been determined that does not result in PL precipitation during cooling, then the cooling and possible filtration steps can be eliminated without loss of activity of the resulting PL-NSAID associated composition.

In another embodiment of the present invention, a method is disclosed including the step of adding a COX-2 inhibitor and a PC to a polar solvent for a dissolution time and at a dissolution temperature, where the dissolution time and dissolution temperature are sufficient to completely dissolve the COX-2 inhibitor and PC. After dissolution with little or no precipitate, the solvent is removed by a solvent removal step for a removal time and at a removal temperature sufficient to remove the solvent below a desired low level, an FDA required level or below a detection limit for the solvent to produce a purified PC-COX-2 associated complex or composition.

Methods for Administrating Purified PL-Associated Complexes

In another embodiment of the present invention, a method is disclosed including the step of administering a pharmaceutically effective amount of a purified PL-sns-NSAID associated complex of this invention to an animal including an human, according to an administration protocol. The administration protocol can include one or a plurality of administering steps, where the each administering step can be selected from the group consisting of an oral administering step, an enteral administering step, a rectal administering step, a topical administering step, an intra-nasal administering step, an intravenous administering step for sterile preparations, an intra-arterial administering step for sterile preparations, a direct tissue injection administering step for sterile preparation and a nasal delivery administering step such as nebulizing into the nose or nose irrigation. Of course, depending on the route of administration and the form of enriched and/or purified PL-sns-NSAID associated complex of this invention, the composition can also include other components adapted to enhance stability (e.g., shelf-life), enhance dispersion, enhance bioavailability, optimize therapeutic activity, etc. For parenteral administration (e.g., intravenous administration, intra-arterial administration, direct tissue administration or a nasal delivery administering step such as nebulizing into the nose or nose irrigation), the enriched and/or purified PL-sns-NSAID associated complex of this invention is generally dispersed, suspended or dissolved in saline or other acceptable isotonic solutions and sterile-filtered prior to delivery as set forth in co-pending U.S. patent application Ser. No. 10/909,748, filed Aug. 2, 2004 and incorporated herein by reference.

Purified PL-NSAID Compositions

In certain embodiments of the present invention, the compositions include a purified PL-sns-NSAID associated complex, where the purified PL-sns-NSAID associated complex has superior GI safety and improved efficacy compared to the sns-NSAID alone or a conventionally prepared PL-sns-NSAID composition.

In certain embodiments of the present invention, the medication including a purified PL-sns-NSAID associated complex of this invention, where the medication is in the form of a soft or hard gelatin capsule, a tablet, a tablet having a water-impermeable coating, a dispersion in a bio-compatible oil, an aqueous suspension or the like.

In certain embodiments of the present invention, the composition comprising an enriched and/or purified PL-NSAID associated complex derived from a polar solvent soluble extract of a PL-NSAID mixture, where the enriched and/or purified PL-NSAID associated complex has superior GI safety and improved efficacy compared to the NSAID alone or a conventionally prepared PL-NSAID composition.

In certain embodiments of the present invention, the medication including a purified PL-NSAID associated complex derived from a polar solvent soluble extract of a PL-NSAID mixture, where the medication has superior GI safety and improved efficacy compared to the NSAID alone or a conventionally prepared PL-NSAID associated complex.

In certain embodiments of the present invention, the composition comprising an enriched and/or purified PL-COX-2 inhibitor associated complex derived from a polar solvent soluble extract of a PL-COX-2 inhibitor mixture, where the enriched and/or purified PL-COX-2 inhibitor associated complex has superior GI safety and improved efficacy compared to the COX-2 inhibitor alone or a conventionally prepared PL-COX-2 inhibitor composition.

In certain embodiments of the present invention, the medication including a purified PL-COX-2 inhibitor associated complex derived from a polar solvent soluble extract of a PL-COX-2 inhibitor mixture, where the medication has superior GI safety and improved efficacy compared to the COX-2 inhibitor alone or a conventionally prepared PL-COX-2 inhibitor associated complex.

For most sns-NSAIDs, the weight ratio that does not result in PL precipitation is at least 1:2 sns-NSAID to PL. For ibuprofen, flurbiprofen or naproxen phospholipid formulations, a weight ratio is at least 1:2 produces associated complexes that are soluble in acetone and produce compositions with properties similar to and often superior, especially in GI toxicity, to the NSAID alone. In most embodiments, the 1:2 weight ratio represents an acceptable material for commercial applications. For aspirin and other salicylic acid derivatives, a weight ratio of 1:2 is effective, but weight ratios between about 1:3 to about 1:4 seem to have somewhat superior GI safety properties.

Method for Screening Compounds

The present invention also relates to a method for screening compounds for their ability to solubilize a PL in a solvent in which the phospholipid has moderate solubility, low solubility or no solubility. The method includes the step of dissolving an amount of a PL in a solvent in which the phospholipid has moderate solubility, low solubility or no solubility, where the amount is sufficient to form a PL precipitate. Once the PL solution having a PL precipitate is formed, adding a compound thereto with stirring and with or without heating. If some or all of the precipitate dissolves, then determining an amount of the compound needed to substantially completely eliminate the precipitate. If a solution is formed having no precipitates, then the solvent is removed to form a composition of the PL and the compound that is soluble in the solvent. The inventor believes that the compounds capable of solubilizing PL are those capable of forming association complexes with the PL. If the compound has biological activity, either pharmaceutical or nutraceutical activity, then the compound may have attributes that alter the efficacy of the compound.

The present invention also relates to an alternate method for screening compounds for their ability of solubilize a PL in a solvent in which the phospholipid has moderate solubility, low solubility or no solubility. The method includes the step of dissolving a compound-to-be-screened in a solvent in which the phospholipid has moderate solubility, low solubility or no solubility. After one prepares the compound solution, an amount of the PL in excess of its solubility in the solvent is added with stirring and with or without heating. If no precipitate forms or if a precipitate forms and then goes away, then determining an amount of the PL needed to result in the formation of a precipitate. If a solution is formed having no precipitates, then the solvent can be removed to form a composition of the PL and the compound that is soluble in the solvent. The inventor believes that the compounds capable of solubilizing PL are those capable of forming association complexes with the PL. If the compound has biological activity, either pharmaceutical or nutraceutical activity, then the compound may have attributes that alter the efficacy of the compound.

Another embodiment of the method of this invention includes dissolving a PL and a pharmaceutically active agent (PA) in a polar solvent. Generally, the polar solvent is heated to facilitate dissolution the PL and PA, with the elevated temperature between room temperature and the boiling point of the solvent chosen. In certain embodiments, the elevated temperature is between about 30° C. and about 90° C. In other embodiments, the elevated temperature is between about 35° C. and about 75° C. In other embodiments, the elevated temperature is between about 40° C. and about 60° C. Dissolution is generally carried out with mixing or stirring to facilitate dissolution and adequate reagent interaction and is continued until the PL and the PA are completely dissolved in the solvent. In certain embodiments, dissolution generally takes between about 10 minutes and about 120 minutes. In other embodiments, dissolution takes between about 15 and 90 minutes, but shorter and longer times can be used depending on the PA, the PL and the polar solvent used.

Once dissolution is complete, the solution is then cooled to a cooling temperature sufficient to permit any PL in excess of an PL-PA associated complex amount to precipitate out of solution. The cooling temperature is generally a temperature lower than the elevated temperature used to completely dissolve the PA and the PL and allows for non-associated PL to be removed from the final composition. The cooling temperature is dependent on the PA used, the PL used and on the solvent used. In certain embodiments of the method of this invention, the cooling temperature is less than the elevated temperature used to dissolve the PA and the PL and is 0° C. or above. In other embodiments of the method of this invention, the cooling temperature is between about room temperature (~25° C.) and about 0° C. In other embodiments of the method of this invention, the cooling temperature is between about 0° C. and about 20° C. In other embodiments o of the method of this invention, the cooling temperature is between about 0° C. and about 10° C. In other embodiments of the method of this invention, the cooling temperature is between about 0° C. and about 4° C.

If a precipitation forms, then the precipitate is removed by any technique known in the art including, without limitation, gravity filtration, vacuum filtration, press filtration, centrifugation, semi-permeable membrane separation, millipore filtration, or other similar method for separating removing precipitates from a supernatant. After cooling, the solution is maintained at the cooling temperature for a cooling time sufficient to allow precipitation of any excess PL and produce a supernatant including a purified PL-PA associated complex. In certain embodiments, the cooling time is between about 10 and about 60 minutes. In other embodiments, the cooling time is between about 15 minutes and about 30 minutes. However, shorter or longer times can be used depending on the solvent and the PL-PA complex. Of course, one of ordinary skill in the art will recognize that the cooling step includes to sub-steps—cooling to a given temperature and holding the resulting composition at the given temperature. Both the rate of cooling and the hold time are subject to variation and are dependent on the PA, PL and solvent used.

The solvent is then removed to produce a purified PL-PA associated complex. Generally, the solvent is removed by evaporation for an evaporation time sufficient to reduce the solvent concentration at or below an acceptably low concentration. In certain embodiments, the evaporation is performed in an inert atmosphere and can be performed in the absence or presence of a vacuum. In other embodiments, the solvent removal technique is rotatory evaporation, which includes liquid rotation in the presence of a vacuum and heating to facilitate solvent removal. In other embodiments, technique for solvent removal is to place the solution in desiccator under a vacuum for an extended period of time until only negligible amounts of solvent can be detected in the composition. In other embodiments, the solvent removal technique is vacuum oven solvent removal, where the oven temperature is generally heat within about ±10° of the boiling point of the solvent. In other embodiments, the solvent removal techniques for solvent is boiling points below about 100° C. is straight distillation, flash distillation or vacuum distillation. In certain embodiments, vacuum distillation is preferred. Straight distillation is always an option, provided, of course, that the distillation temperature does not adversely affect the PA, the PL or the PL-PA associated complex.

While, the inventor has listed several evaporative and distillative process for solvent removal, other known techniques can also be used including, without limitation, spray drying, freeze drying, lyophilizing, or the like.

Of course, any of these solvent removal techniques can be used individually or collectively, provided that the resulting product, which can be a solid, semi-solid, liquid, or oil, is substantially free of solvent or that the solvent concentration in the final product is at or below a desired low value. The desired low solvent value is generally at or below the level set by the FDA in its regulations relating to the purity of pharmaceutical agents. In certain embodiments, the low value is a value at or below the detection limit for an approved analytical technique approved from measuring residual solvent in pharmaceutical compositions.

Once the solvent concentration has been quantitatively reduced or reduces to a desired low value, the final product can be stored for future use or immediately processed into a desired delivery system such as a pill (coated or uncoated), a soft or hard gel capsule, an injectable, an ointment, or the like. If stored, in certain embodiments, the final product is placed in a container under an inert atmosphere.

In one embodiment, the solution is cooled rapidly to a precipitation temperature sufficient to allow any excess PL to precipitate out of solution. The sudden drop in temperature is thought to better facilitation the precipitation of free or non-associated PL producing a superior enriched and/or purified PL-PA associated composition.

While the above screening methods are suitable for determining whether a compounding including pharmaceutically active agent will form associated complexes with PL, the methods are also suitable for manufacturing PL-sns-NSAID associated complexes. However, once the range of sns-NSAID to PL is determined, then the method can simply devolve to mixing the ingredients in the solvent at a dissolution temperature and time sufficient to facilitate complex formation followed by simple solvent removal. Often the resulting composition is a homogeneous oil or an homogeneous viscous fluid.

Suitable Administration Techniques

Suitable administration procedures including, without limitation, oral administration, enteral administration, rectal administration, topical administration, intravenous administration for sterile preparations, intra-arterial administration for sterile preparations, direct tissue administration for sterile preparations, intramuscular administration, sub-dermal micro-pump administration or nasal administration such as nebulizing into the nose or via nasal irrigation. Moreover, one or a plurality of these administrations can be combined into an administration protocol. Thus, the administration protocol can be as simple as a continuous, periodic or intermittent oral administration of a composition of this invention to a complex as intravenous administration, intra-arterial administration, direct tissue administration, intramuscular administration, topical administration, oral administration and nasal administration continuously, periodically or intermittently, where the more complex administration protocols would be suited for battlefield and other emergency situation administration protocol.

Of course, depending on the route of administration, the purified PL-NSAID associated complex of this invention can also include other components adapted to enhance stability (e.g., shelf-life), enhance dispersion, enhance bioavailability, optimize therapeutic activity, etc.

For parenteral administration (e.g., intravenous administration, intra-arterial administration, intramuscular administration, or direct tissue administration), the enriched and/or purified PL-NSAID associated complex of this invention is generally suspended in saline or other acceptable isotonic solution and sterile-filtered prior to delivery as set forth in co-pending U.S. patent application Ser. No. 10/909,748, filed Aug. 2, 2004 and incorporated herein by reference.

The compositions of this invention comprise enriched and/or purified PL-NSAID associated complexes having superior GI safety and improved efficacy compared to the PA alone or a conventionally prepared PL-NSAID composition. In certain embodiments, the compositions of this invention include one or a plurality of PLs and one or a plurality of NSAIDs or a chemically related pharmaceutical agents such as acetaminophen, that have solubility in a polar solvent such as acetone. Well suited pharmaceutical agents for use in the compositions of this have associated with their administration adverse side effects such as GI ulceration, pain, dyspepsia, heartburn, mucositis, inflammation, erosions, bleeding and/or perforation, or other adverse GI side effects or limited bio-availability.

In certain embodiments, the medications of this invention include a purified PL-sns-NSAID associated complex of this invention, where the medication is in the form of a soft or hard gelatin capsule, a tablet, a tablet having a water-impermeable coating, a dispersion in a bio-compatible oil, an aqueous suspension or the like.

Suitable Reagents

Suitable phospholipids for use in this invention include, without limitation, a phospholipid of general formula:

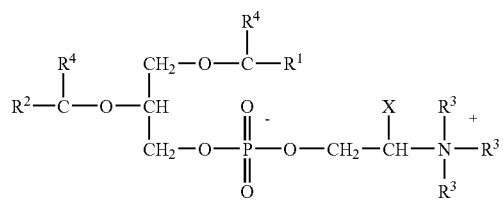

where $R^1$ and $R^2$ are saturated or unsaturated substitutions ranging from 8 to 32 carbon atoms; $R^3$ is H or $CH_3$, and X is H or COOH; and $R^4$ is $=O$ or $H_2$ or mixtures or combinations thereof. Phospholipid compounds in certain embodiments of the present invention found to be particularly useful practice are dilinoleoyl phosphatidylcholine (DLL-PC), dipalmitoyl phosphatidylcholine (DPPC) and egg phosphatidylcholine (Egg-PC or $PC_e$). In DPPC, a saturated phospholipid, the saturated aliphatic substitution $R^1$ and $R^2$ are $CH_3$—$(CH_2)_{14}$, $R^3$ is $CH^3$ and X is H. In DLL-PC, an unsaturated phospholipid, $R^1$ and $R^2$ are $CH_3$—$(CH_2)_4$—CH=CH—$CH_2$—CH=CH—$(CH_2)_7$, $R^3$ is $CH_3$ and X is H. In Egg PC, which is a mixture of unsaturated phospholipids, $R^1$ primarily contains a saturated aliphatic substitution (e.g., palmitic or stearic acid), and $R^2$ is primarily an unsaturated aliphatic substitution (e.g., oleic or arachidonic acid) or mixtures or combinations thereof.

Exemplary examples of zwitterionic phospholipid, without limitation, phosphatidylcholines such as phosphatidylcholine (PC), dipalmitoylphosphatidylcholine (DPPC), other disaturated phosphatidylcholines, phosphatidylethanolamines, phosphatidylinositol, phosphatidyl serines sphingomyelin or other ceramides, or various other zwitterionic phospholipids, phospholipid containing oils such as lecithin oils derived from soy beans, dimyristoyl phosphatidylcholine, distearoylphosphatidylcholine, dilinoleoylphosphatidylcholine (DLL-PC), dipalmitoylphosphatidylcholine (DPPC), soy phophatidylchloine (Soy-PC or $PC_S$) and egg phosphatidycholine (Egg-PC or $PC_E$). In Soy-PC, which in addition to the saturated phospholipids (palmitic acid and stearic acid) is a mixture of unsaturated phospholipids, [oleic acid, linoleic acid and linolenic acid]. In certain embodiments, the zwitterionic phospholipid include, without limitation, dipalmitoyl phosphatidylcholine, phosphatidyl choline, or mixtures or combinations thereof.

Suitable selective and nonselective non-steroidal, anti-inflammatory drugs (sns-NSAIDs) include, without limitation, nonselective non-steroidal, anti-inflammatory drug (NSAIDs) and selective non-steroidal, anti-inflammatory drug (NSAIDs) or COX-2 inhibitors or mixtures or combinations thereof.

Suitable non-steroidal, anti-inflammatory drug (NSAIDs) include, without limitation, Propionic acid drugs such as Fenoprofen calcium (Nalfon®), Flurbiprofen (Ansaid®), Suprofen. Benoxaprofen, Ibuprofen (prescription Motrin®), Ibuprofen (200 mg. over the counter Nuprin, Motrin 1B®), Ketoprofen (Orduis, Oruvall®), Naproxen (Naprosyn®), Naproxen sodium (Aleve®, Anaprox®, Aflaxen®), Oxaprozin (Daypro®), or the like; Acetic acid drug such as Diclofenac sodium (Voltaren®), Diclofenac potassium (Cataflam®), Etodolac (Lodine®), Indomethacin (Indocin®), Ketorolac tromethamine (Acular®, Toradol® intramuscular), Ketorolac (oral Toradol®), or the like; Ketone drugs such as Nabumetone (Relafen®), Sulindac (Clinoril®), Tolmetin sodium (Tolectin®). or the like; Fenamate drugs such as Meclofenamate sodium (Meclomen®), Mefenamic acid (Ponstel®), or the like; Oxicam drugs such as Piroxicam (Dolibid®), or the like; Salicylic acid drugs such as salicylic acid, magnesium salicylate, Diflunisal (Feldene®), Aspirin, or the like; Pyrazolin acid drugs such as Oxyphenbutazone (Tandearil®), Phenylbutazone (Butazolidin®), or the like; acetaminophen (Tylenol®), or the like, or mixtures or combinations thereof. In certain embodiments, the NSAIDs are ibuprofen, aspirin, salicylic acid, naproxen, indomethacin, diclofenac, piroxicam, fluobiprofen, ketoprofen and mixtures or combinations thereof.

Suitable COX-2 inhibitors for using in this invention include, without limitation, celecoxib, meloxicam, lumiracoxib, meloxicam, piroxicam, or newly approved COX-2 inhibitors or mixtures or combinations thereof.

Suitable polar solvents for use in the present invention include, without limitation, ketones such as acetone, methylethyl ketone (MEK), methylbutyl ketone, methylisobutyl ketone or the like, acetates such as methylacetate, ethylacetate, propylacetate, isopropyl acetate, butylacetate, isobutylacetate, or the like, nitriles such as acetonitrile or the like, ethers such as diethylether, tetrahydrofuran, or the like, formates such as ethylformate, N,N-dimethylacetamide, N,N-dimethylformamide, N-methylpyrrolidone, nitromethane, chlorinated hydrocarbons such as carbon tetrachloride, chloroform, 1,2-dichloroethane, 1,1-dichlorethene, 1,2-dichloroethene, dichloromethane, 1,1,1-trichloroethane or the like, or mixture or combinations thereof. In certain embodiments, the solvent is acetone, but the choice of solvent will depend on the pharmaceutical agent and the phospholipid chosen. Thus, the solvent must dissolve the pharmaceutical agent readily, while the phospholipid must have a moderate or low solubility in the absence of the pharmaceutical agent. In certain embodiments, the phospholipid has a higher solubility at an elevated temperature and a lower solubility at a lower temperature.

Suitable adjuvants, helping additives, include, without limitation, adjuvants that control pH and secondary therapeutic adjuvants including, without limitation: (1) anti-inflammatory agents such as antihistamines, corticosteroids, or the like, or mixtures or combinations thereof; (2) anti-microbial agents such as eugenol, guaiacol, zephiran chloride, or the like, or mixtures or combinations thereof; (3) antibiotic agents such as bacitracin, neomycin sulfate, gentamicin sulfate, erythromycin or the like, or mixtures or combinations thereof; (4) hemostatics agents such as oxidized cellulose, thrombin, carboxymethylcellulose, or the like, or mixtures or combinations thereof; (5) anesthetic agents such as procaine, xylocaine, carbocaine, or the like, or mixtures or combinations thereof; (6) antifungal agents such as benzoic acid, salicylic acid, amphotericin B, miconazole, nistatin, toinaftate or the like or mixtures or combinations thereof; (7) other additives that can improve or enhance the therapeutic benefit of the compositions of this invention without interfering with the inhibiting activity of the enzyme inhibitors; or mixtures or combinations thereof or any of the above groups' listed adjuvants.

Adjuvants that control pH by neutralizing fecal components known to exacerbate the enzymatic insult of exposed or involved tissues, include, without limitation, effective concentrations of inorganic and organic buffers, (pK's from 2.0 to 6.0), to control pH between about 3.0 and about 7.0 such as carbonates, maleates, borates, citrates, adipates, or the like, or mixtures or combinations thereof. Controlling pH between about 3.0 and about 6.0 will prevent ammonia emission, neutralize bile acid/salt activity and help minimize enzyme activities. Weakly basic anion exchange resins of agarose, dextran, cellulose and polystyrene to sequester or augment neutralization of bile salt/acid and contribute to pH control, or mixtures or combinations thereof.

Suitable chemical excipients to solubilize, stabilize, emulsify and/or suspend the primary (enzyme inactivators), and secondary chemical or therapeutic components (adjuvants), include, without limitation, emulsifiers, surfactants, suspending agents, or mixtures or combinations thereof.

Suitable emulsifiers include, without limitation: (1) monomolecular films such as laurates, sorbitans, or the like, or mixtures or combinations thereof; (2) multimolecular films such as Acacia, gelatin, or the like, or mixtures or combinations thereof; (3) solid particle films such as bentonite or the like, or mixtures or combinations thereof; (4) surfactants such as natural or synthetic, anionic, cationic or nonionic surfactants, or mixtures or combinations thereof; or (5) combinations or mixtures of the above-listed emulsifiers.

Suitable topical preparation include, without limitation, ointments, emulsions, suspensions, powders, or the like.

Suitable emulsifiers include, without limitation: (1) monomolecular films such as laurates, sorbitans, or the like, or mixtures or combinations thereof; (2) multimolecular films such as Acacia, gelatin, or the like, or mixtures or combinations thereof; (3) solid particle films such as bentonite or the like, or mixtures or combinations thereof; (4) surfactants such as natural or synthetic, anionic, cationic or nonionic surfactants, or mixtures or combinations thereof; or (5) combinations or mixtures of the above-listed emulsifiers.

Suitable bio-compatible emulsifying agent include, without limitation, any ionic or non-ionic emulsifying agent or surfactants approved for human or animal consumption or internal use. Exemplary examples include acetylated monoglycerides, aluminum salts of fatty acids, Arabinogalactan, Bakers Yeast Glycan, Calcium carbonate, Calcium salts of fatty acids, Carob bean gum (locust bean gum), Curdlan, Diacetyl tartaric acid esters of mono- and diglycerides of edible fats or oils, or edible fat-forming fatty acids, Dioctyl sodium sulfosuccinate, Disodium phosphate (X-ref-Sodium phosphate, mono-, di-, & tri-), Ethoxylated mono- and diglycerides, Eucheuma cottonii extract, Eucheuma spinosum extract, Fatty acids, salts of (aluminum, calcium, magnesium, potassium, and sodium), Food starch esterified with n-octenyl succinic anhydride treated with beta-amylase, Furazolidone, Furcelleran, Furcelleran, salts of ammonium, calcium, potassium, or sodium, Ghatti gum, Gigartina extracts, Glyceryl-lacto esters of fatty acids, Hexitol oleate, Hydroxylated lecithin, Hydroxypropyl cellulose, Hydroxypropyl methylcellulose, Lactylated fatty acid esters of glycerol and propylene glycol, Lactylic esters of fatty acids, Lecithin, hydroxylated lecithin, Methyl ethyl cellulose, Mono- & diglycerides of edible fats or oils, or edible fat forming acids, Monoisopropyl citrate, Monosodium phosphate derivatives of mono- & diglycerides of edible fats or oils, or edible fat-forming fatty acids, Myrj 45 (polyoxyethylene 8-stearate), Ox bile extract, Pectins (including pectin modified), Polyethylene glycol (400) dioleate, Polyglycerol esters of fatty acids, Polyoxyethylene glycol (400) mono- & di-oleates, Polysorbate 60 (Polyoxyethylene (20) sorbitan monostearate), Polysorbate 65 (Polyoxyethylene (20) sorbitan tristearate), Polysorbate 80 (Polyoxyethylene (20) sorbitan monooleate), Potassium salts of fatty acids, Propylene glycol alginate (Propylene glycol ester of alginic acid), Propylene glycol mono- & di-esters of fats & fatty acids, Rapeseed oil, fully hydrogenated, superglycerinated, Sodium acid pyrophosphate, Sodium aluminum phosphate, Sodium hypophosphite, Sodium lauryl sulfate, Sodium metaphosphate, Sodium methyl sulfate, Sodium pectinate, Sodium salts of fatty acids, Sodium stearoyl lactylate, Sodium sulfo-acetate derivatives (mono- & di-glycerides), Sorbitan monooleate, Sorbitan monostearate, Succinylated monoglycerides, Succistearin (stearoyl propylene glycol hydrogen succinate), Sucrose acetate isobutyrate (SAIB), Sucrose fatty acid esters, Sulfated butyl oleate, Trisodium phosphate, Xanthan gum, or the like or mixtures or combinations thereof.

Suitable neutral lipids include, without limitation, any neutral lipids such as the triglyceride. For a partial listing of representative neutral lipids, such as the triglycerides, reference is specifically made to U.S. Pat. Nos. 4,950,656 and 5,043,329. Both saturated and unsaturated triglycerides may be employed in the present compositions, and include such triglycerides as tripalmitin (saturated), triolein and trilinolein (unsaturated). However, these particular triglycerides are listed here for convenience only, and are merely representative of a variety of useful triglycerides, and is further not intended to be inclusive.

Non-limiting examples of suitable biocompatible, biodegradable polymers, include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof or combinations or mixtures thereof. In certain embodiments, the preferred biodegradable polymers are all degraded by hydrolysis.

Typically, the polymers will either be surface erodible polymers such as polyanhydrides or bulk erodible polymers such as polyorthoesters. Poly(l-lactic acid) (PlLA), poly(dl-lactic acid) (PLA), poly(glycolic acid) (PGA), polycaprolactones, copolymers, terpolymer, higher poly-monomer polymers thereof, or combinations or mixtures thereof. In certain preferred embodiments, the polymers are preferred biocompatible, biodegradable polymers. The biodegradable copolymers are lactic acid and glycolic acid copolymers sometimes referred to as poly(dl-lactic-co-glycolic acid) (PLG). In certain preferred embodiments, the co-monomer (lactide:glycolide) ratios of the poly(DL-lactic-co-glycolic acid) are between about 100:0 to about 50:50 lactic acid to glycolic acid. In certain preferred embodiments, the co-monomer ratios are between about 85:15 and about 50:50 lactic acid to glycolic acid. Blends of PLA with PLG, preferably about 85:15 to about 50:50 PLG to PLA, are also used to prepare polymer materials.

PLA, PlLA, PGA, PLG and combinations or mixtures or blends thereof are among the synthetic polymers approved for human clinical use. They are presently utilized as surgical suture materials and in controlled release devices, as well as in other medical and pharmaceutical applications. They are biocompatible and their degradation products are low molecular weight compounds, such as lactic acid and glycolic acid, which enter into normal metabolic pathways. Furthermore, copolymers of poly(lactic-co-glycolic acid) offer the advantage of a large spectrum of degradation rates from a few days to years by simply varying the copolymer ratio of lactic acid to glycolic acid.

To enhance bio-degradation of the polymers used in biological application, the compositions of the present invention can also include the addition of enzymes that can facilitate the biodegradation of the polymers used in the composition. In certain preferred embodiments, the enzymes or similar reagents are proteases or hydrolases with ester-hydrolyzing capabilities. Such enzymes include, without limitation, proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase or the like. The inclusion of an appropriate amount of such a degradation enhancing agent can be used to regulate implant duration.

Suitable bio-compatible oils include, without limitation, any oil approved for human or animal consumption by the FDA including natural oils such as plant or animal oils or their derivatives or synthetic oils and especially natural oil that are rich in phospholipids such as lecithin oils from soy beans. Exemplary examples of such oils include, essential oils, vegetable oils an hydrogenated vegetable oils, animal oils such as peanut oil, canola oil, avocado oil, safflower oil, olive oil, corn oil, soy bean oil, sesame oil, vitamin A, vitamin D, vitamin E, fish oils, or the like.

The formulation or compositions of this invention can also include other chemicals, such as anti-oxidants (e.g., Vitamin A, C, D, E, etc.), trace metals and/or polyvalent cations (aluminum, gold, copper, zinc, calcium, etc.), surface-active agents and/or solvents (e.g., propylene glycol/PPG, dimethy sulfoxide/DMSO, medium chain triglycerides/MCT, etc.), non-toxic dyes and flavor enhancers may be added to the formulation as they are being prepared to improve stability, fluidity/spreadability, permeability, effectiveness and consumer acceptance.

Discussion of Experimental Details of Embodiments of the Invention

The inventor has found that by combining either a purified phosphatidylcholine (PC) or a PC-enriched lecithin oil with acetone in the presence of an non-steroidal, anti-inflammatory drug (NSAID) such as ibuprofen, whether the NSAID is added first, second or simultaneous with the PC to the acetone, remarkably decreases the amount of material that precipitates from the acetone after dissolution and cooling. Generally, the PC and NSAID are dissolved in the acetone at a temperature between about 40° C. and about 60° C. for a time between about 15 and about 90 minutes, where shorter or longer times are permitted depending on the PC. After the PC and NSAID are dissolved in the acetone, the acetone solution is cooled to a temperature between about 0° C. and about 4° C. by placing the vessel containing the solution in an ice bath for about 15 to about 30 minutes, where shorter or longer times are permitted depending on the PC and the NSAID. The resulting mixture is then centrifuged, and the supernatant is decanted. The acetone precipitable material is then collected and weighed. The supernatant is then dried in an oven at an elevated temperature between about 60° C. and about 110° C. for a sufficient period of time to remove residual solvent, where the sufficient period of time is generally between 1 hour and several days.

Using this procedure, it was determined that systematically increasing the weight ratio of ibuprofen to a lecithin oil containing 35% PC, (P35 SB, purchased from American Lecithin, Oxford, Conn.), from a ratio of 0.0:1.0 (no ibuprofen) to 2.5:1.0 in 0.5 increments resulted in a step-wise decrease in acetone precipitable material from 50% to <8% as shown in FIG. 1. Thus, the presence of ibuprofen prevented the PC from precipitating out of acetone producing a purified PC-ibuprofen associated complex.

Figure 2:
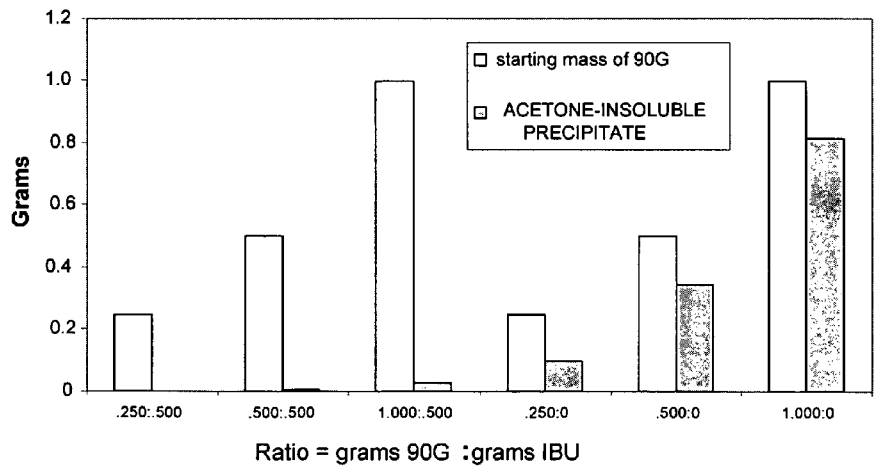
FIG. 2 depicts a plot of acetone precipitables versus a series of weight ratios of 90G (the source of PC) to ibuprofen.

In another in vitro experiment, the amount of ibuprofen was kept constant at 0.5 g to which was added increasing amounts from 0.25 g to 1.0 g of purified soy (>90% pure) PC (Phosal 90G, purchased from American Lecithin, Oxford, Conn.). It can be seen in FIG. 2 that no acetone precipitable material was detected until a weight ratio of 90G:ibuprofen of 1.0:0.5 g was reached. Thus, when using purified soy lecithin phospholipids, a purified PC-ibuprofen associated composition is optimally achieved at a weight ratio of 2:1 (PC:ibuprofen).

In Vivo Examples

Based upon these experiments, we performed two in vivo experiments to evaluate the GI safety and therapeutic effectiveness of the resulting 2:1 weight ratio, purified PC:ibuprofen complex. It should be noted that acetone was exhaustively removed before the purified PC-ibuprofen complex was evaluated in a rodent test system.

Figure 3:
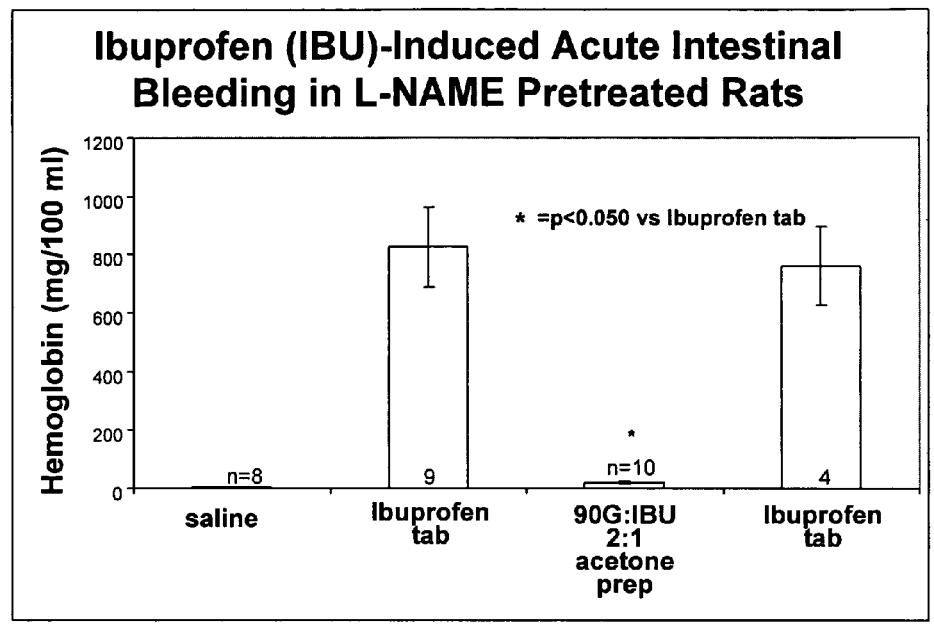
FIG. 3 depicts a plot of induced acute (L-NAME) intestinal bleeding in rats data comparing ibuprofen alone, acetone dissolved ibuprofen and a purified PC-ibuprofen composition of this invention.

In the first in vivo example, we used an acute rodent model of NSAID-induced GI bleeding in rats treated with the nitric oxide synthetase inhibitor, N-nitro-L-arginine methyl ester (L-NAME) as described in Lichtenberger L M, Wang Z-M, Romero J J, Ulloa C, Perez J C, Giraud M-N, Barreto J C. Non-steroidal anti-inflammatory drugs (NSAIDs) associate with zwitterionic phospholipids: Insight into the mechanism and reversal of NSAID-induced gastrointestinal injury. *Nature Medicine* 1: 154-158, 1995, incorporated herein by reference. The results presented in FIG. 3 indicate that using comparable concentrations of ibuprofen (250 mg/kg), the acetone prepared PC (90G)-ibuprofen complex induced a remarkable (>95%) reduction in GI bleeding (as determined by measuring hemoglobin in an intestinal perfusate) than seen in the ibuprofen control or a group of animals that were administered ibuprofen that was previously exposed to acetone, and the solvent subsequently removed by exhaustive evaporation.

Figure 4:
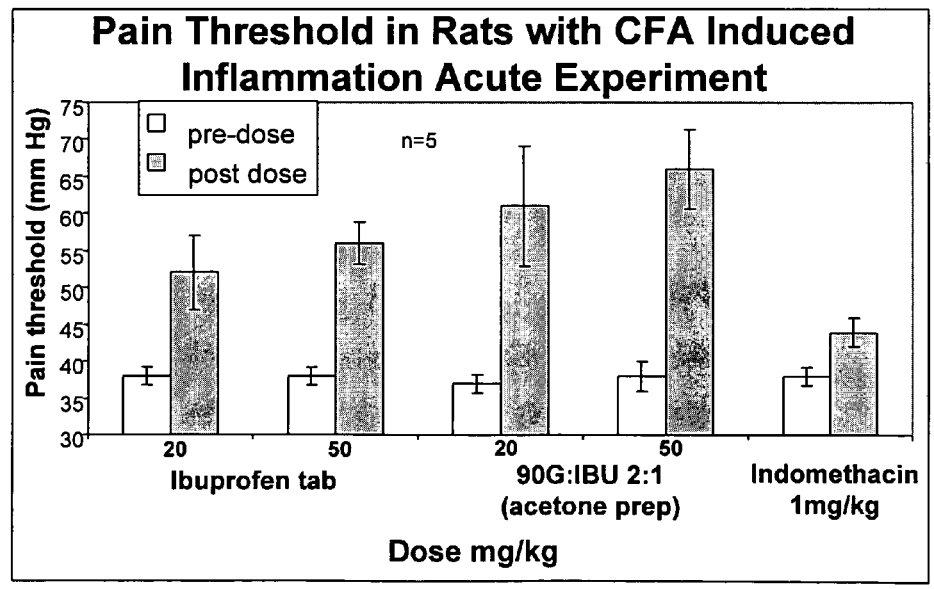
FIG. 4 depicts a plot of pain threshold data in rats that received an injection of 0.1 mL of CFA in a hind paw four days NSAID testing with ibuprofen, indomethacin, and a purified PC-ibuprofen composition of this invention.

In the second in vivo experiment, we compared the analgesic activity of the acetone preparation of PC-ibuprofen to that of ibuprofen alone (at doses of 20 and 50 mg/kg) in rats and compared the response to a sub-threshold dose of indomethacin (1 mg/kg). The measurements were made on rats, in which 0.1 mL of Complete Freund's Adjuvant (CFA) was subcutaneously injected into the dorsal surface of the left hindpaw, 4 days previously to increase the affected paw's sensitivity to pressure. On the day of the experiment, a baseline (pre-dose) pain pressure threshold was measured using our modification of the Randall-Sellito technique (see Lichtenberger L M, Ulloa C, Vanous A L, Romero J J, Dial E J, Illich P A, Walters E T. Zwitterionic phospholipids enhance aspirin's therapeutic activity, as demonstrated in rodent model systems. *JPET* 1996; 277: 1221-1227), and then the procedure repeated two hours after dosing of the test agents. FIG. 4 reveals that both unmodified ibuprofen and the acetone prepared PC-ibuprofen induced an apparent dose-dependent increase in pain pressure threshold, whereas the sub-threshold dose of indomethacin had no effect. Furthermore, this index of the analgesic activity indicated that the therapeutic activity of the acetone-prepared PC-ibuprofen was comparable to and/or superior to that of unmodified ibuprofen.

Acute Gastric Ulcer Model in Rodents

Figure 8:
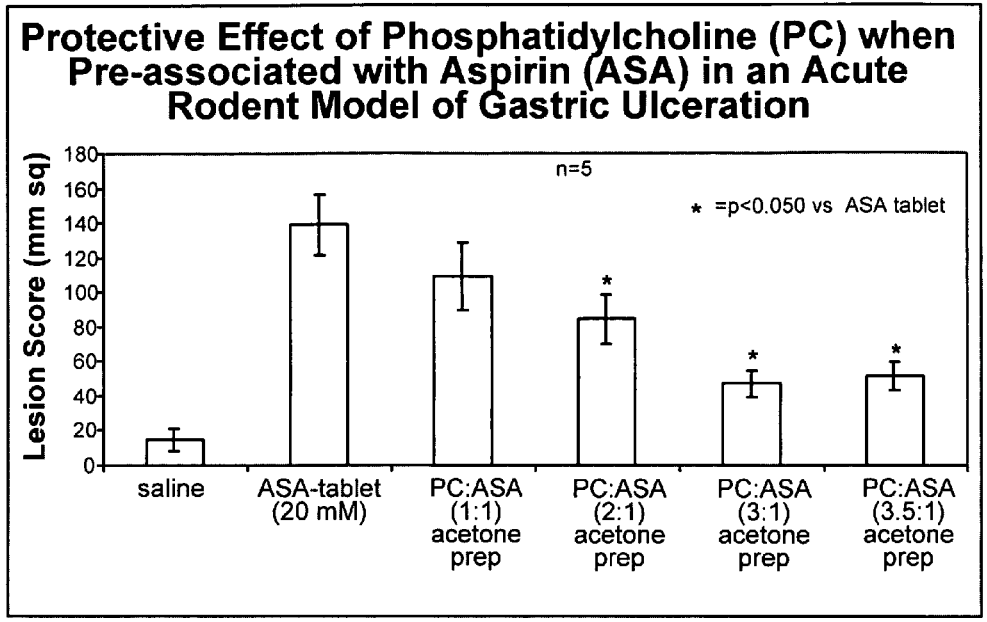
FIG. 8 depicts results of protective effect of phosphatidylcholine (PC) when pre-associated with Aspirin (ASA) in an acute rodent model of gastric ulceration comparing saline, ASA from tablets, 1:1 PC-ASA prepared using acetone, 2:1 PC-ASA prepared using acetone, 3:1 PC-ASA prepared using acetone, and 3.5:1 PC-ASA prepared using acetone.
Figure 9:
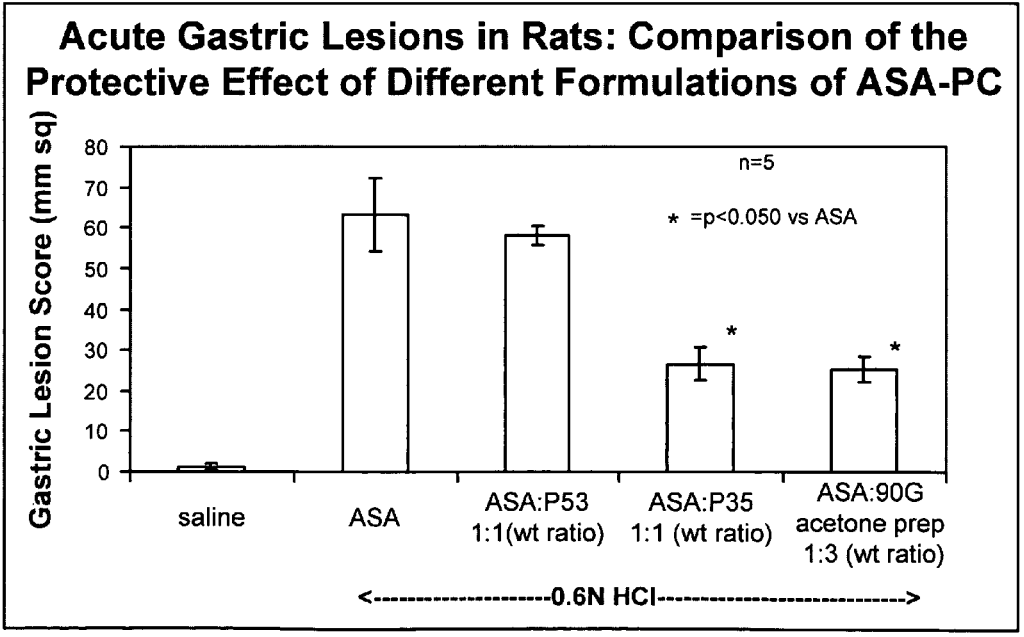
FIG. 9 depicts results of acute gastric lesions in rats comparing saline, ASA (aspirin), 1:1 ASA:P53, 1:1 ASA:P35 and 1:3 ASA:90G prepared using acetone.
Figure 10:
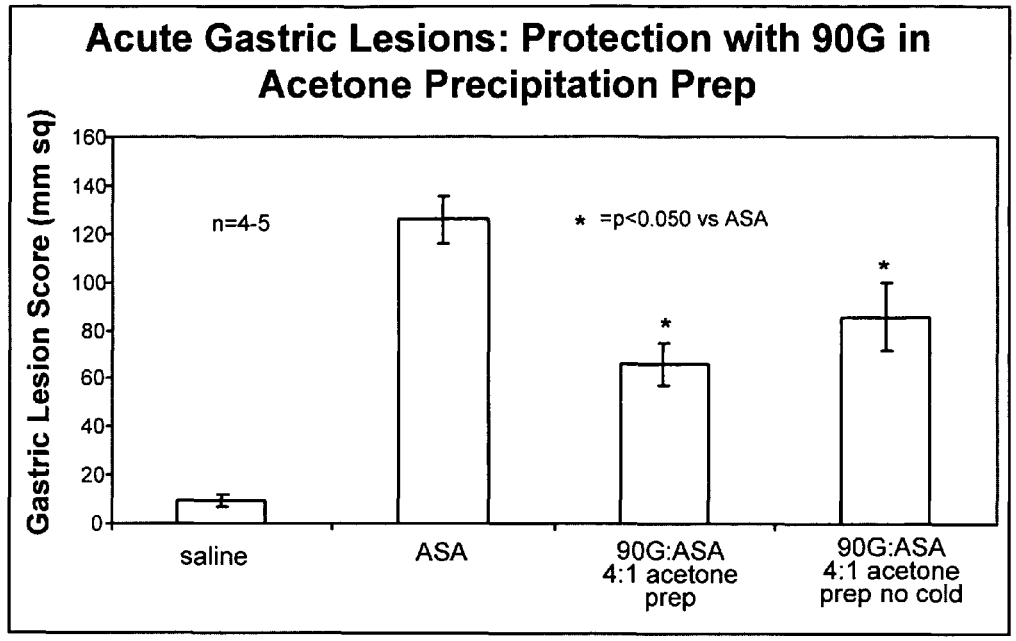
FIG. 10 depicts results of acute gastric lesions in rats comparing saline, ASA (aspirin), 1:4 ASA:90G prepared using acetone with cooling and 1:4 ASA:90G prepared using acetone without cooling.

In the second in vivo experiment, in this study, aspirin was combined with Phosal 35 SB, a soy lecithin oil, containing 35% PC, P53 is a lecithin oil containing 53% PC or Phospholipon 90G, a soy lecithin containing >90% PC and intragastrically administered to fasted rats at an aspirin dose of 18 mg/kg, where the NSAID:lecithin oil weight ratio was systematically varied from 1:0.5, to 1:1, to 1:2 as shown in FIGS. 8-10. In addition, other groups of rats received an equivalent dose of aspirin in the absence of the lecithin oil, or an equivalent volume of saline. Forty five minutes later all animals were intragastrically challenged with 1 mL of 0.6 N HCl, and 15 min later, the animals were euthanized and their stomachs opened and the gastric lesions scored by an established method.

Chronic Model of NSAID-Induced GI Toxicity

In this protocol, rats received a subcutaneous injection (via a 20 gauge needle attached to a 1 mL syringe) of 0.2 mL of Complete Freund's Adjuvant (CFA; Sigma Chemical, St. Louis, Mo.) into the left hind ankle inducing acute joint inflammation. The rats then were randomly assigned to the study groups, and immediately began a regimen of dosing treatments with either saline vehicle, Ibuprofen (50-75 mg/kg, b.i.d.), or PC-Ibuprofen (50-75 mg NSAID/kg, b.i.d.) for 4-5 consecutive days. At the completion of the study period, the rats were weighed and euthanized by $CO_2$ inhalation followed by bilateral thoracotomy. We evaluated the toxicity of our ibuprofen test preparations by measuring changes in body weight, hematocrit values, presence of intestinal perforations and concentration of hemoglobin in the GI perfusate. In addition, tissue samples were collected from the inflamed joint in order to perform a myeloperoxidase assay, evaluating neutrophil activity of the inflamed tissue. Lastly, ankle thickness measurements were taken to demonstrate the anti-inflammatory action of the NSAID preparations and a modified Randall and Selitto pain test was utilized to show analgesic activity. Additional details of the Randall and Selitto and modified Randall and Selitto pain tests can be found in Lichtenberger L M, Ulloa C, Vanous A L, Romero J J, Dial E J, Illich P A, Walters E T. Zwitterionic phospholipids enhance aspirin's therapeutic activity, as demonstrated in rodent model systems. *JPET* 1996; 277: 1221-1227; Lichtenberger L M, Romero J J, DeRuijter W M J et al. Phosphatidylcholine association increases the anti-inflammatory and analgesic activity of ibuprofen in acute and chronic rodent models of inflammation: relationship to alterations in bioavailability and cyclooxygenase-inhibitory activity. *JPET* 298:279-287, 2001 and Randall L O, Selitto J J. A method of measuring analgesic activity of inflamed tissue. *Arch Int Pharmacodyn* 1957; 111: 409-419, incorporated herein by reference.

The following parameters were measured to assess NSAID-induced GI toxicity.

Delta Body Weight

The change in body weight over the dosing period was calculated by subtracting the body weights of the rats on the final day of the study from their initial pre-treatment weights. This is called the 'delta' weight.

Hematocrit Values

The hematocrit was measured by withdrawing rat blood via a cardiac puncture into a capillary tube and then spinning it down and measuring the red blood cell fraction over the total serum fraction.

GI Perfusate

During tissue collection, the distal half of the small intestine was flushed with 3 ml of cold saline, and the hemoglobin concentration in the collected perfusate was measured as previously described and additional details can be found in Lichtenberger L M, Graziani L A, Dial E J, Butler B D, Hills B A. Role of surface-active phospholipids in gastric cytoprotection. Science 1983; 219:1327-29, incorporated herein by reference.

Fecal Hemoglobin

Fecal pellets were collected at the time of euthanasia, homogenized in water and their hemoglobin concentration measured as previously described and additional details can be found in Lichtenberger L M, Graziani L A, Dial E J, Butler B D, Hills B A. Role of surface-active phospholipids in gastric cytoprotection. Science 1983; 219:1327-29, incorporated herein by reference.

Intestinal Perforations

The distal half of the small intestine was opened longitudinally and examined for the presence of perforations and/or adhesions by an observer that was blinded to which experimental group the tissue was collected.

Assessment of the NSAID Anti-Inflammatory and Analgesic Activity

The therapeutic activity of the test-NSAID preparations was evaluated by measuring ankle thickness, myeloperoxidase activity and the sensitivity of the inflamed paw to pressure using techniques briefly outlined below, that were described in more detail in Lichtenberger L M, Romero J J, DeRuijter W M J et al. Phosphatidylcholine association increases the anti-inflammatory and analgesic activity of ibuprofen in acute and chronic rodent models of inflammation: relationship to alterations in bioavailability and cyclooxygenase-inhibitory activity. *JPET* 298:279-287, 2001, incorporated herein by reference.

Ankle Thickness

The ankle thickness of the rats locally injected with CFA was measured using a caliper by a blinded observer as previously described.

Analgesic Activity as Assessed by Randall Selitto Pain Sensitivity Test

To assess NSAID-induced analgesia we employed a modification of the technique of Randall and Selitto as described previously. Briefly, this is accomplished by placing the hindpaw of a conscious rat, that is contained in a plexiglass restraining cage on the stage of an Analgesymeter (Life Sciences Instruments, Woodlands Hills, Calif.) that applies increasing pressure (mm Hg) overtime to the paw of a rat using a small stainless steel probe with a blunt end. We defined the "pain pressure threshold" as the lowest pressure at which the rat senses pain as indicated by either digit extension or an attempt to withdraw its paw from the probe, as assessed by a "blinded" observer. Myeloperoxidase Activity The inflamed joint tissue was carefully dissected from animal at necropsy, homogenized by Polytron for approximately 30 sec in 1 ml of 0.5% hexadecyltrimethylammonium bromide in 50 mM potassium phosphate buffer. The homogenate was then frozen (in liquid nitrogen) and thawed three times and microfuged, and the supernatant was collected. A 10 to 20-μl sample of the supernatant was added to microwell ELISA plates, followed by the addition of 200 μl of tetramethylbenzidine substrate in accordance to a previously described method. Additional detail can be found in Lichtenberger L M, Ulloa C, Vanous A L, Romero J J, Dial E J, Illich P A, Walters E T. Zwitterionic phospholipids enhance aspirin's therapeutic activity, as demonstrated in rodent model systems. *JPET* 1996; 277: 1221-1227 and Suzuki K, Ota H, Sasagawa S, Sakatani T, Fujikura T. Assay method for myeloperoxidase in human polymorphonuclear leukocytes. *Anal Biochem* 1983; 132: 345-352, incorporated herein by reference. Peroxidase was added to wells in buffer at a dose range between 0 and 25 ng/ml in place of the supernatant. After an incubation period of 15 min in the dark at room temperature, the plates were read on an ELISA Plate Reader (Precision Microplate Reader, Molecular Devices, Menlo Park, Calif.) at a wavelength of 650 nm.

Statistical Analysis

Inter-group comparison was performed by analysis of variance followed by Fisher LSD test for significance with $p<0.05$ as the limit for statistical significance between groups.

EXAMPLES OF THE INVENTION

Example 1

In this example, 1.0 gram of triple strength soy lecithin. (containing 33-35% PC, Phosal 35 SB from American Lecithin) was dissolved in 15 mL of acetone (containing 0, 0.5, 1.0, 1.5, 2.0 and 2.5 g of ibuprofen-acid) in pre-tared 50 ml centrifuge tubes. The tubes were warmed to a temperature of about 40° C. to about 45° C. for 15-30 minutes until all the PL was dissolved. At this point cold acetone (4° C.) was added to the tubes to the 40 mL mark and tubes are place in an ice bath for 15 minutes during which the solution was stirred. The tubes are then centrifuged at 2,000 rpm for 15 minutes, and the supernatant was decanted. The residue at the bottom of the tube was then broken up with a stirring rod and an additional 40 mL of chilled acetone were added to the tubes. The tubes were then placed in an ice bath for an additional 15 minutes, and centriguged as described above and the supernatants were decanted. The tubes were then placed in a horizontal position and place in an oven set at 105° C. for several day until constant weights were obtained. The results presented in FIG. 1 demonstrate that the amount of PL precipitated by acetone was reduced by adding increasing amounts of ibuprofen (IBU) to the polar solvent from 50% (0 IBU) to <8% at a weight ratio IBU:P35 of 2:1 or greater.

Example 2

In this example, 0.5 g of ibuprofen were predissolved in pre-tared tubes containing 15 mL of acetone to which increasing amounts (0.25 g, 0.5 g, 1.0 g) of purified (>90%) soy PC (Phosal90 G, American Lecithin) was added. In a separate set of tubes increasing amounts of PC were added to pre-tared tubes containing 15 mL of acetone and no ibuprofen. The tubes were then treated as described above to dissolve and then precipitate the PC (by adjusting the temperature from 40° C. to 4° C., and the acetone precipitable materials were measured by weight. The results which are graphically depicted in FIG. 2 indicate that in the presence of ibuprofen little or no purified PC precipitated in acetone until the weight ratio of PC:IBU exceeded 2:1. These results suggest that at this ratio almost all the available PC was present in the acetone phase as a PC-ibuprofen complex.

Example 3

In this example, PC-ibuprofen was prepared as described above, in which the weight ratio of 90G:ibuprofen was adjusted to 2:1 to assure optimal formation of the complex. In this experiment, however, the acetone soluble phase was collected, and the acetone was removed by evaporation under a stream of $N_2$ gas. The tubes containing the PC-ibuprofen material were then transferred to desiccator and left under vacuum for several days. A similar process to that described above was performed to unmodified ibuprofen-acid that was dissolved in acetone, and then the solvent was exhaustively removed by evaporation.

In order to evaluate the GI safety of the acetone-prepared PC-ibuprofen, we employed a previously described method of assessing intestinal bleeding in rats that are treated with the NO synthetase-inhibitor, L-NAME, to increase their sensitivity to the GI side-effects of NSAIDs. This was accomplished by subcutaneously injecting fasted male, Sprague Dawley rats (150-200 g) with L-NAME (20 mg/kg) 1 hour before, and 1 and 6 hours after rats intragastrically received 1 mL of the NSAID test solutions as a solution or suspension. In this experiment, fasted rats were intragastrically administered saline (control) or the ibuprofen test solutions (either generic ibuprofen, acetone prepared PC-ibuprofen, or acetone prepared ibuprofen) at a dose of 200 mg/kg suspended in deionized distilled water. The rats were then returned to their cages and provided ad libitum access to food and water, and euthanized 16 hours after NSAID administration by $CO_2$ inhalation, at which time the distal half of the intestine was dissected and flushed with 10 mL of cold saline and the perfusate collected for hemoglobin analysis as previously described. The results depicted in FIG. 3, demonstrate that in comparison to the generic ibuprofen acid, that was either untreated or exposed to acetone, both of which induced severe acute intestinal bleeding in rats (>800 mg % hemoglobin), rats treated with an equivalent dose of the acetone prepared PC-ibuprofen sustained little or no intestinal bleeding (<25 mg % of hemoglobin). This indicates that the acetone prepared PC-NSAID was remarkably safer (>95% reduction in GI bleeding) than unmodified ibuprofen.

Example 4

In this example, PC-ibuprofen was prepared as described above, in which the weight ratio of 90G:ibuprofen was adjusted to 2:1 to assure optimal formation of the complex. In this experiment, however, the acetone soluble phase was collected, and the acetone was removed by evaporation under a stream of $N_2$ gas. The tubes containing the PC-ibuprofen material were then transferred to desiccator and left under vacuum for several days. A similar process to that described above was performed to ibuprofen-acid that was dissolved in acetone, and then the solvent was exhaustively removed by evaporation.

In this experiment, we evaluated the analgesic activity of the test material using a rodent model system previously described in detail. This was accomplished by initially inducing inflammation of a hind paw of male Sprague Dawley rats by subcutaneously injecting 0.1 mL of Complete Freund's Adjuvant (Sigma Chemical Co. St. Louis, Mo.) into the doral surface of the left hind paw. To assess NSAID-induced analgesia four days after the induction of joint inflammation, we employed a modification of the technique of Randall and Selitto as previously described. Briefly, this was accomplished by placing the hind paw of a fasted, conscious rat, that is contained in a plexiglass restraining cage on the stage of an Analgesymeter (Life Sciences Instruments, Woodlands Hills, Calif.) that applies increasing pressure (mm Hg) overtime to the paw of a rat using a small stainless steel probe with a blunt end. We defined the "pain pressure threshold" as the lowest pressure at which the rat senses pain as indicated by either digit extension or an attempt to withdraw its paw from the probe, as assessed by a "blinded" observer.

In this experiment, whose results are depicted in FIG. 4, we initially measured a pre-dose pain pressure threshold, and then immediately intragastrically dosed the fasted rats with either 20 or 50 mg/kg of either generic ibuprofen or the acetone prepared PC-ibuprofen. For comparison, we also intragastrically administered a group of rats with a sub-threshold dose (1 mg/kg) of the NSAID, indomethacin, that was suspended in 1% methyl cellulose. Two hours later, the pain pressure threshold was repeated, and it can be seen that both generic ibuprofen and the acetone prepared PC-ibuprofen complex appeared to induce a dose-dependent increase in pain pressure threshold which is indicative of analgesic activity. In comparison is the non-significant response recorded in rats that received the sub-threshold dose of indomethacin. Since the rats that received the acetone prepared PC-ibuprofen sustained a significant increase in pain pressure threshold, that was equivalent to or greater than the response of rats that received an equivalent dose of generic ibuprofen, one can conclude that the therapeutic activity of ibuprofen was not altered by the acetone preparation procedure and may, in fact, have been enhanced.

Example 5

In this example, the GI protective properties using the L-NAME model for a PC-ibuprofen associated composition of this invention compared to ibuprofen (IBU), the sodium salt of ibuprofen, and four conventionally prepared ibuprofen/PC formulations were analyzed.

Figure 5:
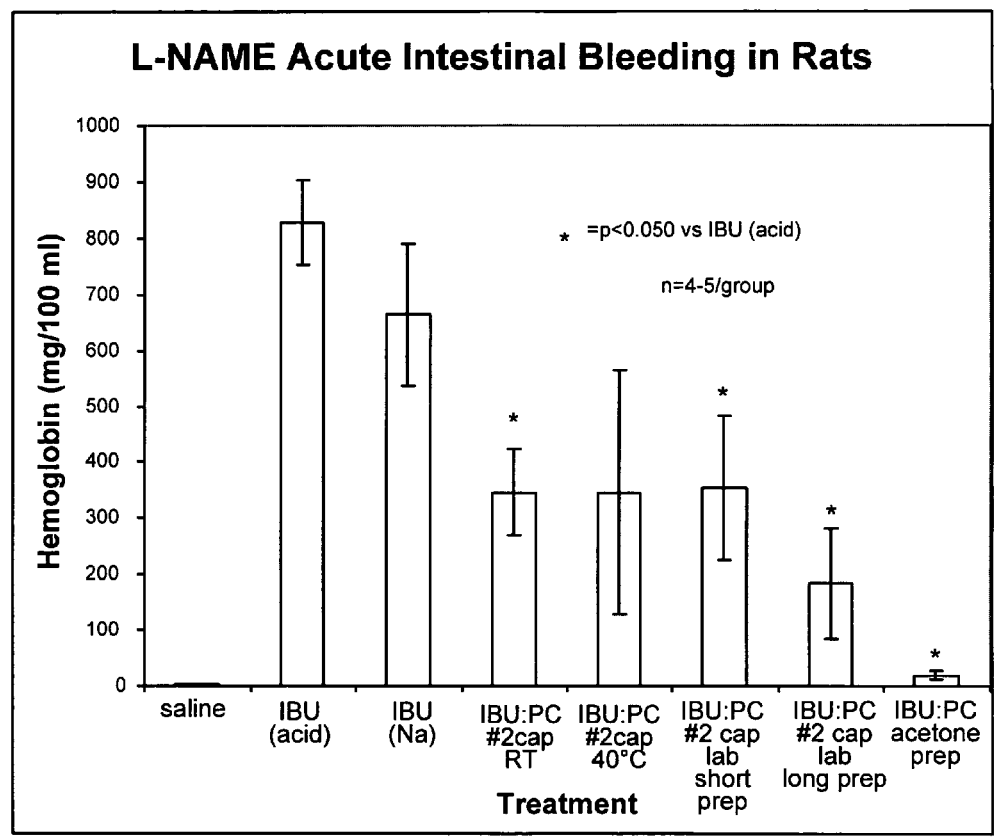
FIG. 5 depicts a plot of induced acute (L-NAME) intestinal bleeding in rats data comparing ibuprofen alone, the sodium salt of ibuprofen alone, four oil-based PC-ibuprofen compositions and a purified PC-ibuprofen composition of this invention.

Referring now to FIG. 5, a plot of the GI protective properties of: Bar 1—saline; Bar 2—IBU; Bar 3—NaIBU (ibuprofen sodium salt); Bar 4—IBU/lecithin oil containing 35% PC composition stored for 6 months at room temperature; Bar 5—IBU/lecithin oil containing 35% PC composition stored at 40° C. for 3 months and room temperature for the remaining 3 month period prior to animal testing; Bar 6—freshly prepared IBU/lecithin oil containing 35% PC composition (10 minute, 40° C. mix time); Bar 7—freshly prepared IBU/lecithin oil containing 35% PC composition (30 minute, 40° C. mix time); and Bar 8—purified PC-IBU associated composition of this invention prepared using acetone as the solvent (last bar). It is clear that the purified PC-IBU associated composition of this invention substantially out performed all the other IBU formulations, showing GI protective properties similar to that of saline.

Chronic Model to Assess NSAID Induced GI Toxicity and Therapeutic Activity

In this protocol, rats received a subcutaneous injection (via a 20 gauge needle attached to a 1 mL syringe) of 0.2 mL of Complete Freund's Adjuvant (CFA; Sigma Chemical, St. Louis, Mo.) into the left hind ankle inducing acute joint inflammation. The rats then were randomly assigned to the study groups, and immediately began a regimen of dosing treatments with either saline vehicle, Ibuprofen (50-75 mg/kg, b.i.d.), or PC-Ibuprofen (50-75 mg NSAID/kg, b.i.d.) for 4-5 consecutive days. At the completion of the study period, the rats were weighed and euthanized by $CO_2$ inhalation followed by bilateral thoracotomy. We evaluated the toxicity of our ibuprofen test preparations by measuring changes in body weight, hematocrit values, presence of intestinal perforations and concentration of hemoglobin in the GI perfusate. In addition, tissue samples were collected from the inflamed joint in order to perform a myeloperoxidase assay, evaluating neutrophil activity of the inflamed tissue. Lastly, ankle thickness measurements were taken to demonstrate the anti-inflammatory action of the NSAID preparations and a modified Randall and Selitto pain test was utilized to show analgesic activity. Additional details of the Randall and Selitto and modified Randall and Selitto pain tests can be found in Lichtenberger L M, Ulloa C, Vanous A L, Romero J J, Dial E J, Illich P A, Walters E T. Zwitterionic phospholipids enhance aspirin's therapeutic activity, as demonstrated in rodent model systems. *JPET* 1996; 277: 1221-1227; Lichtenberger L M, Romero J J, DeRuijter W M J et al. Phosphatidylcholine association increases the anti-inflammatory and analgesic activity of ibuprofen in acute and chronic rodent models of inflammation: relationship to alterations in bioavailability and cyclooxygenase-inhibitory activity. *JPET* 298:279-287, 2001 and Randall L O, Selitto J J. A method of measuring analgesic activity of inflamed tissue. *Arch Int Pharmacodyn* 1957; 111: 409-419, incorporated herein by reference.

These two procedures were employed to establish the bioavailability and overall therapeutic activity of the two NSAID preparations. In the experiments evaluating the topical anti-inflammatory and analgesic activity of the test formulations, CFA was injected into the hindpaw as described above, and 3 days later the ankle thickness and pain pressure threshold were analyzed (as outlined below) to record a baseline (pre-treatment) reading. Immediately afterward the test drugs were topically administered to the affected paw, at the described doses, either as an oil or dissolved in propylene glycol vehicle. And this application procedure was performed twice daily for the subsequent 3-5 day period, and the anti-inflammatory and analgesic activity assessed at these time points by an observer in a blinded fashion.

Preparation of PC-Ibuprofen Formulation

The PC-ibuprofen formulation was prepared by dissolving the required concentration of ibuprofen (or a different test NSAID) in acetone containing twice the concentration of Phospholipon 90G (American Lecithin), containing ~93-96% PC. The NSAID and PC (at a 1:2 weight ratio) were incubated in acetone at 40° C. until dissolved and the polar solvent was then removed by evaporation first under a stream of nitrogen and then under vacuum. The final product being an oil and comprising a purified PC-NSAID associated complex. The product was then either administered to the test animals directly, or resuspended in water or another vehicle (as indicated). To facilitate the intragastric delivery of this formulation at a particular ibuprofen dose range, the required volume was suspended in water and vortexed prior to intragastric administration. For topical delivery, the product was administered directly (undiluted) to the affected paw or resuspended in propylene glycol (pg).

Example 6

Figure 6:
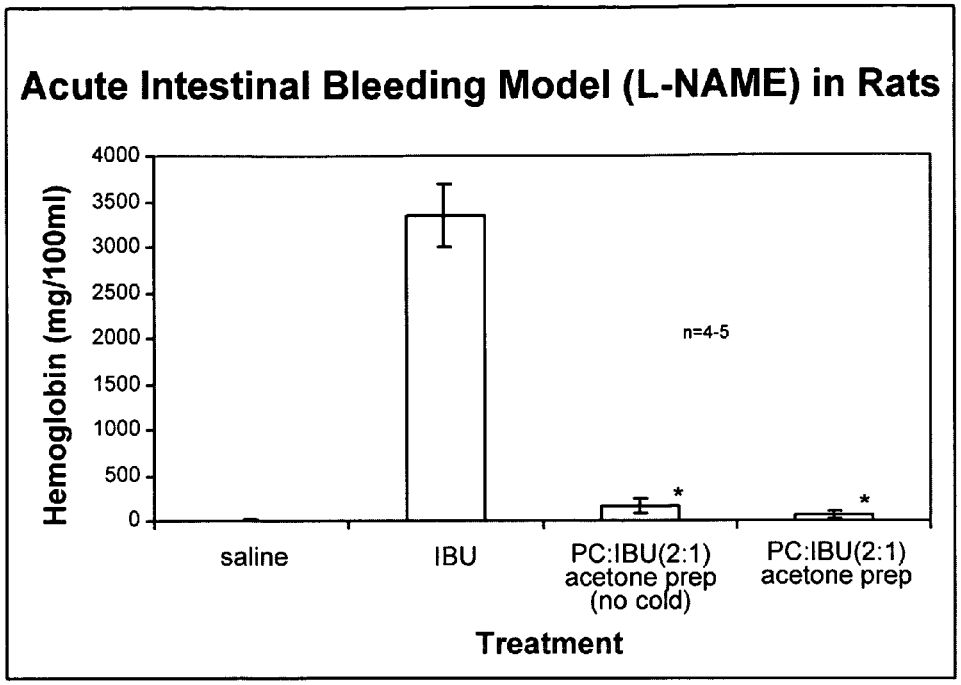
FIG. 6 depicts results from an acute intestinal bleeding model (L-NAME) in rats comparing saline, ibuprofen (IBU), purified PC:IBU in a 2:1 weight ratio prepared using acetone without cooling, and purified PC:IBU in a 2:1 weight ratio prepared using acetone with cooling.

Referring now to FIG. 6, results are shown from an acute intestinal bleeding model (L-NAME) study in rats as described above comparing saline, ibuprofen (IBU), purified PC:IBU in a 2:1 weight ratio prepared using acetone without cooling, and purified PC:IBU in a 2:1 weight ratio prepared using acetone with cooling. Clearly, the acetone preparations show significant reductions in hemoglobin regardless of whether the acetone preparation includes a cooling step.

Example 7

Figure 7:
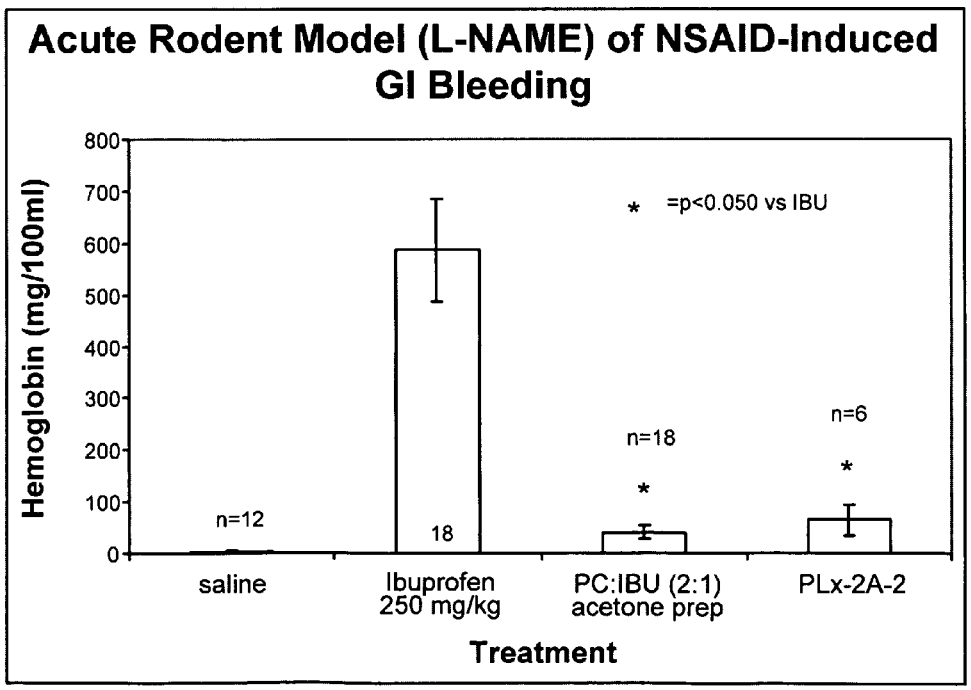
FIG. 7 depicts results from an acute intestinal bleeding model (L-NAME) in rats comparing saline, ibuprofen, purified PC:IBU in a 2:1 weight ratio prepared using acetone, and a IBU/lecithin oil containing 35% PC composition, PLx-2A-2.

Referring now to FIG. 7, results from another acute intestinal bleeding model (L-NAME) study in rats comparing saline, ibuprofen, purified PC:IBU in a 2:1 weight ratio prepared using acetone, and a IBU/lecithin oil containing 35% PC composition, Plx-2A-2. In the study, the acetone prepared PC:IBU formulation showed better and/or comparable results than an oil based PC:IBU (PLx-2A-2) material prepared according to the procedures set forth in U.S. patent application Ser. No. 10/433,454, filed Nov. 6, 2003.

Example 8

Referring now to FIG. 8, results of the protective effect of phosphatidylcholine (PC) when pre-associated with Aspirin (ASA) in an acute rodent model of gastric ulceration comparing saline is shown for ASA from tablets, 1:1 PC-ASA prepared using acetone, 2:1 PC-ASA prepared using acetone, 3:1 PC-ASA prepared using acetone, and 3.5:1 PC-ASA prepared using acetone. The study was carried out in accordance with the experimental description given above. The study indicates that the ratio of 3:1 PC to ASA gave the best protection of the ASA formulations tested.

Example 9

Referring now to FIG. 9, results of acute gastric lesions in rats comparing saline, ASA (aspirin), 1:1 ASA:P53, 1:1 ASA:P35 and 1:3 ASA:90G prepared using acetone are shown. Again, the study was carried out in accordance with the experimental description given above. The study indicates the 1:3 ASA:PC acetone preparation has efficacy similar to an oil based 1:1 ASA:P35 material prepared according to the procedures set forth in U.S. patent application Ser. No. 10/433,454, filed Nov. 6, 2003, and both are superior to ASA and ASA:PC53.

Example 10

Referring now to FIG. 10, results of acute gastric lesions in rats comparing saline, ASA (aspirin), 1:4 ASA:90G prepared using acetone with cooling and 1:4 ASA:90G prepared using acetone without cooling. Again, the study was carried out in accordance with the experimental description given above. The study indicates that the two acetone preparation prepared with and without the cooling step performed similarly and superior to ASA alone.

Example 11

Figure 11:
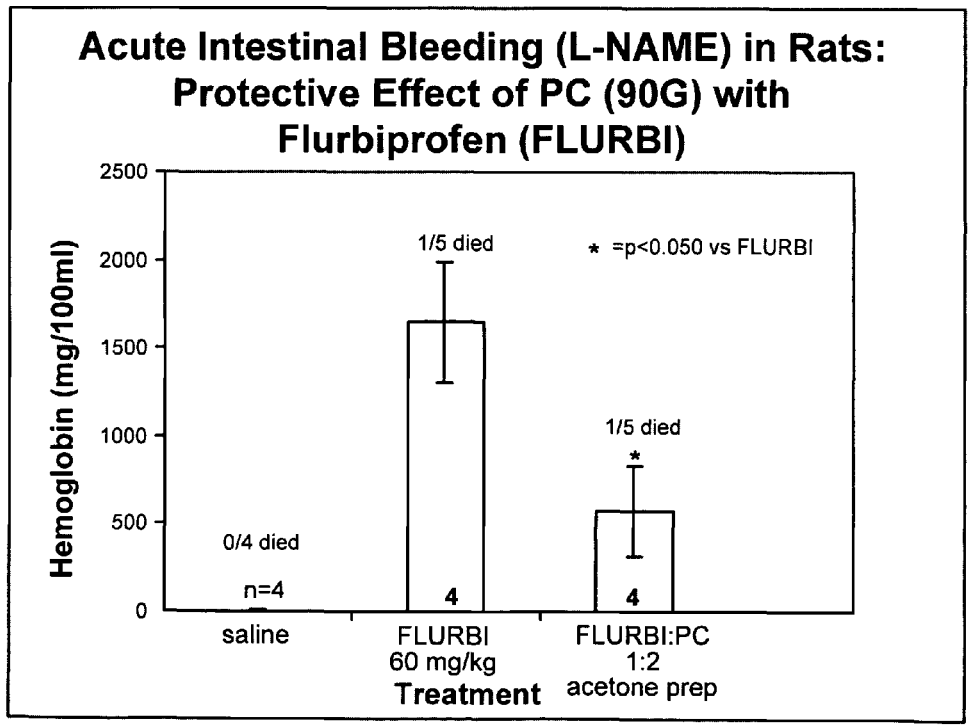
FIG. 11 depicts results of acute gastric lesions in rats comparing saline, flurbiprofen (FURIB) and 1:2 FURIB:PC prepared using acetone.

Referring now to FIG. 11, results of acute gastric lesions in rats comparing saline, flurbiprofen (FURIB) and 1:2 FURIB: PC prepared using acetone. Again, the study was carried out in accordance with the experimental description given above. The study indicates flurbiprofen:PC prepared using acetone is superior to flurbiprofen alone.

Example 12

Figure 12:
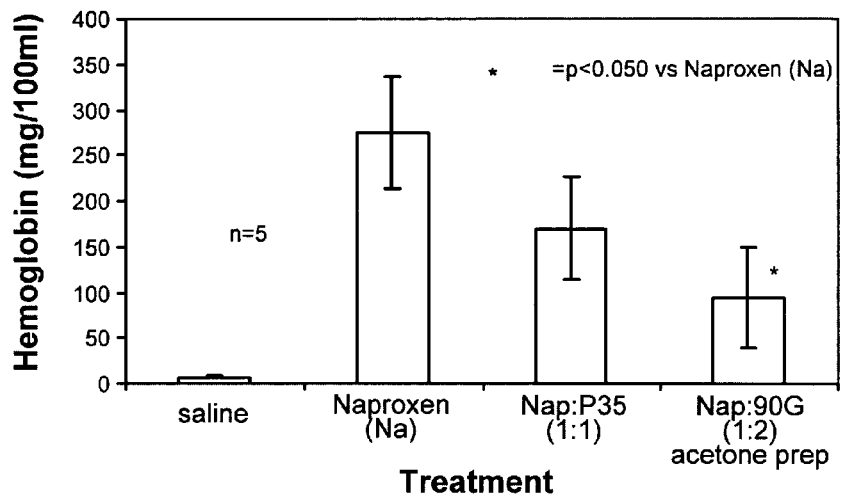
FIG. 12 depicts results of acute gastric lesions in rats comparing saline, Naproxen (Nap) sodium salt, 1:1 Nap:P35 and 1:2 Nap:90G prepared using acetone.

Referring now to FIG. 12, results of acute gastric lesions in rats comparing saline, Naproxen (Nap) sodium salt, 1:1 Nap: P35 and 1:2 Nap:90G prepared using acetone. Again, the study was carried out in accordance with the experimental description given above. The study indicates the 1:2 Nap:90G prepared using acetone is superior either to Nap alone or a 1:1 Nap:P35 prepared according to the procedures set forth in U.S. patent application Ser. No. 10/433,454, filed Nov. 6, 2003.

Example 13

Figure 13:
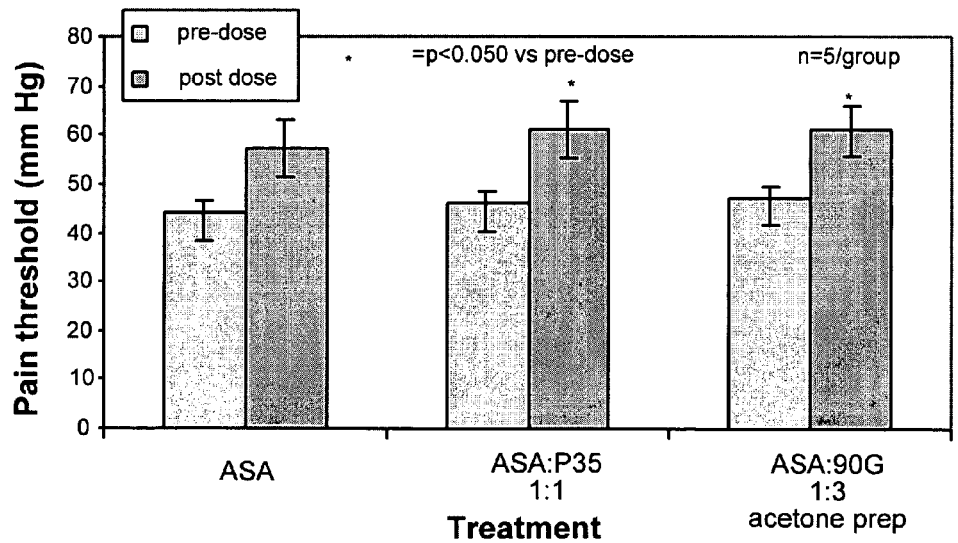
FIG. 13 depicts results of a pain threshold on CFA induced inflammation in rats using a Randall Siletto procedure comparing ASA (aspirin), 1:1 ASA:P35 and 1:3 ASA:90G prepared using acetone.

Referring now to FIG. 13, results of a pain threshold on CFA induced inflammation in rats using a Randall Siletto procedure comparing ASA (aspirin), 1:1 ASA:P35 and 1:3 ASA:90G prepared using acetone. Again, the study was carried out in accordance with the experimental description given above. The study indicates all three ASA formulations performed similarly.

Example 14

Referring now to FIGS. 14A-G, the effects of various ibuprofen (IBU) formulations on rats treated with CFA to induce joint inflammation were studied. The rats were administered saline with no CFA treatment, saline after CFA treatment, IBU (ibuprofen) after CFA treatment, 1:2 IBU:90G prepared using acetone, and a IBU/lecithin oil containing 35% PC composition, PLx-2A-2. The PLx-2A-2 material was prepared according to the procedures set forth in U.S. patent application Ser. No. 10/433,454, filed Nov. 6, 2003. Again, the study was carried out in accordance with the experimental description given above.

Figure 14A:
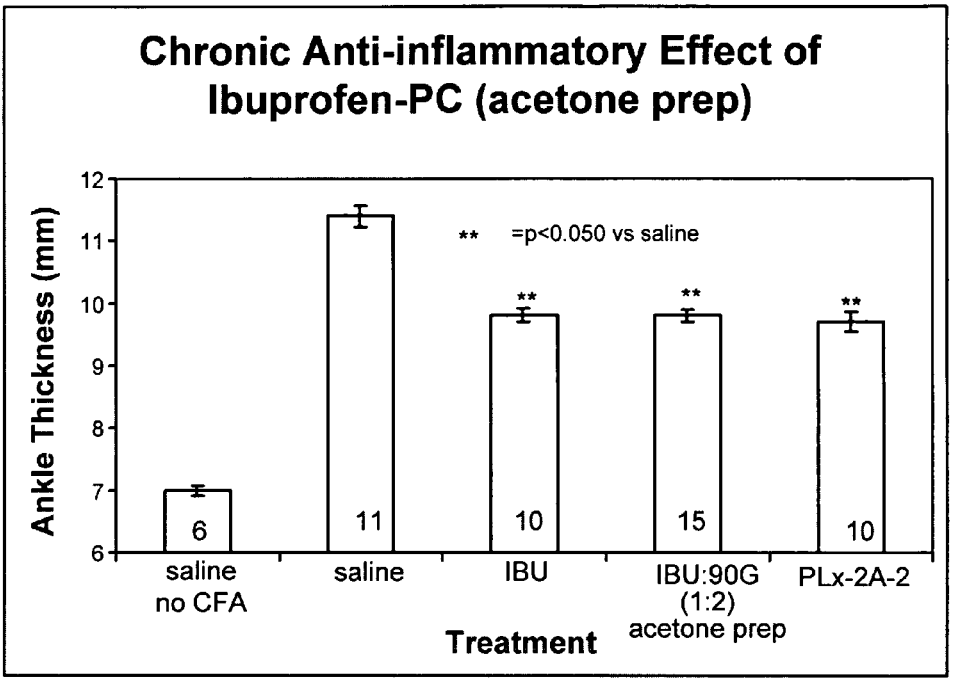
FIG. 14A depicts results of chronic anti-inflammatory effect on ankle thickness in rats treated with CFA of saline with no CFA treatment, saline after CFA treatment, IBU (ibuprofen) after CFA treatment, 1:2 IBU:90G prepared using acetone, and a IBU/lecithin oil containing 35% PC composition, PLx-2A-2.
Figure 14B:
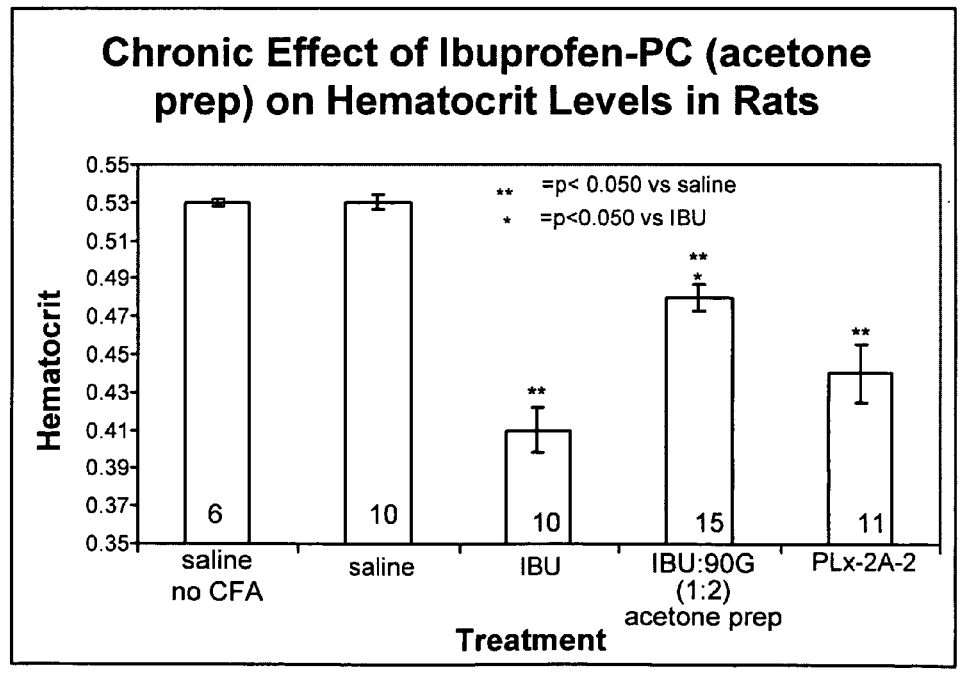
FIG. 14B depicts results of chronic effect on hematocrit levels in rats treated with CFA of saline with no CFA treatment, saline after CFA treatment, IBU (ibuprofen) after CFA treatment, 1:2 IBU:90G prepared using acetone, and a IBU/lecithin oil containing 35% PC composition, PLx-2A-2.
Figure 14C:
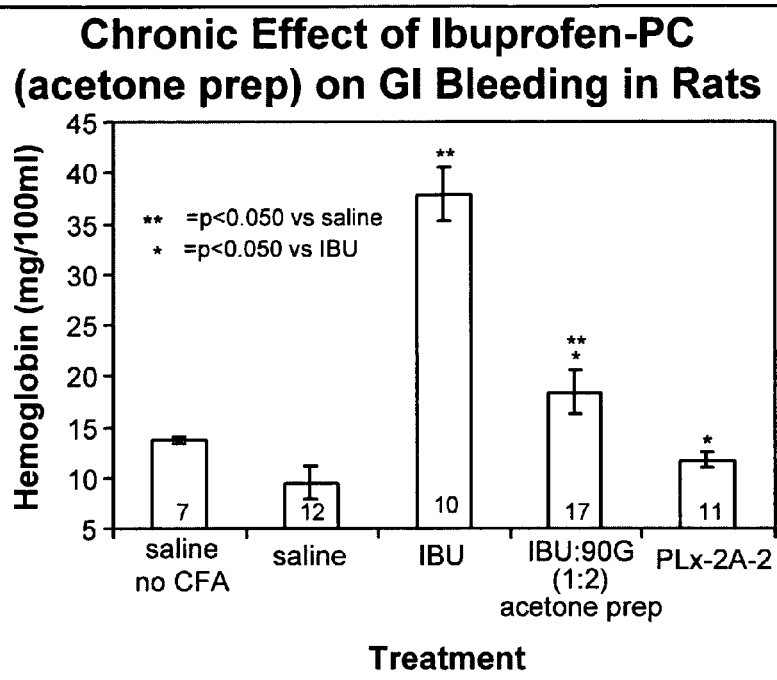
FIG. 14C depicts results of chronic effect on GI bleeding in rats treated with CFA of saline with no CFA treatment, saline after CFA treatment, IBU (ibuprofen) after CFA treatment, 1:2 IBU:90G prepared using acetone, and a IBU/lecithin oil containing 35% PC composition, PLx-2A-2.
Figure 14D:
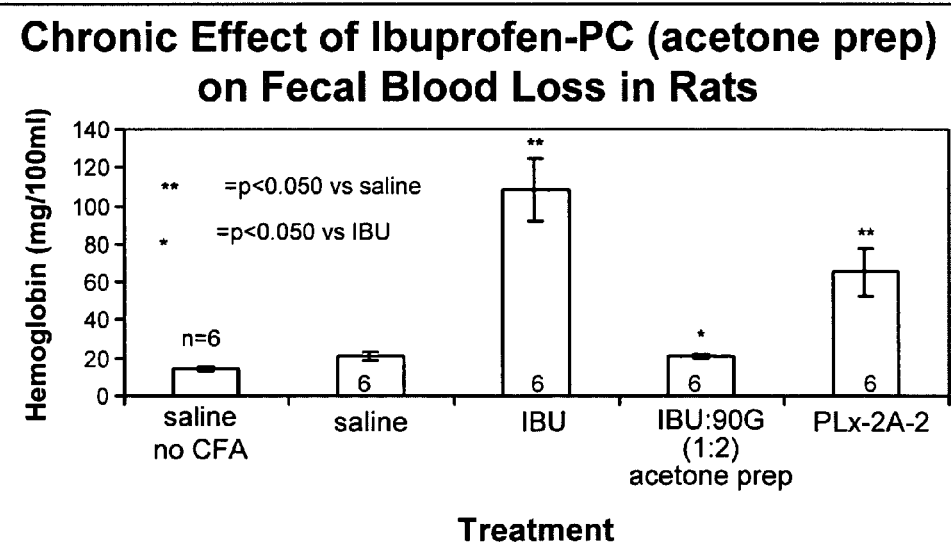
FIG. 14D depicts results of chronic effect on fecal blood loss in rats treated with CFA of saline with no CFA treatment, saline after CFA treatment, IBU (ibuprofen) after CFA treatment, 1:2 IBU:90G prepared using acetone, and a IBU/lecithin oil containing 35% PC composition, PLx-2A-2.
Figure 14E:
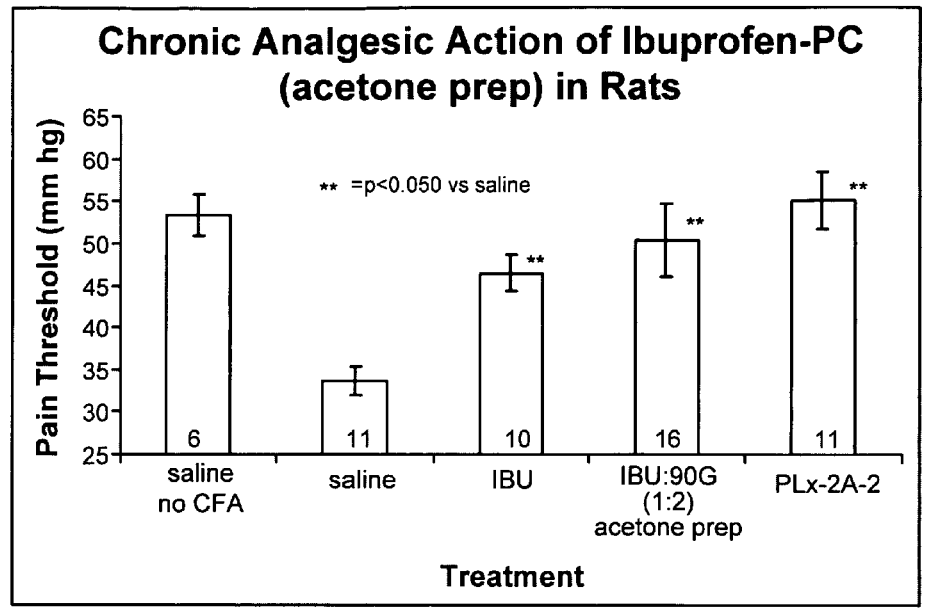
FIG. 14E depicts results of chronic analgesic action in rats treated with CFA of saline with no CFA treatment, saline after CFA treatment, IBU (ibuprofen) after CFA treatment, 1:2 IBU:90G prepared using acetone, and a IBU/lecithin oil containing 35% PC composition, PLx-2A-2.
Figure 14F:
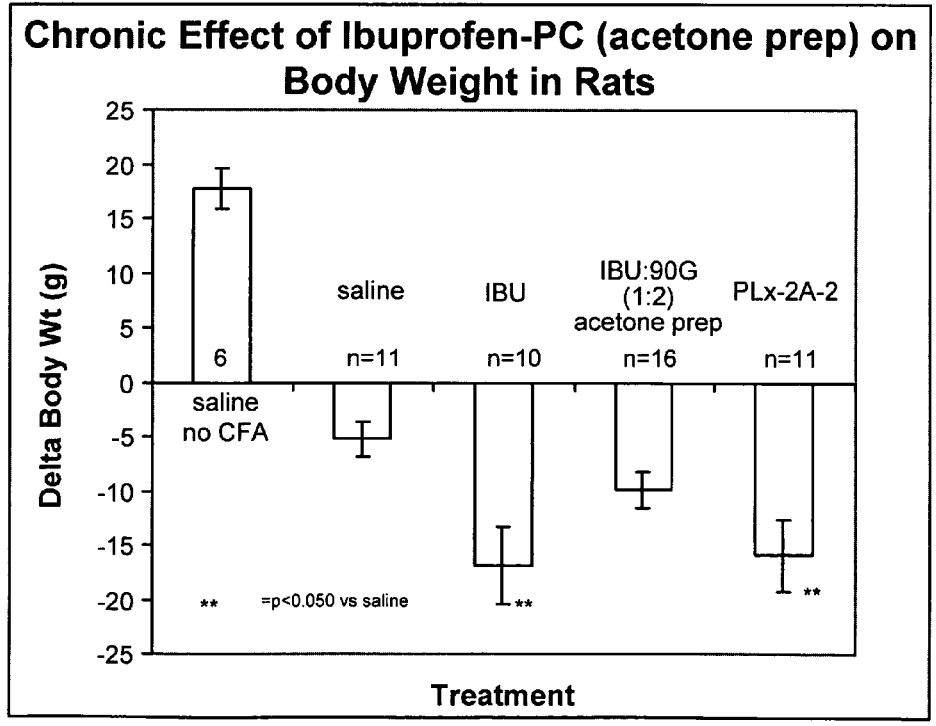
FIG. 14F depicts results of chronic NSAID treatment on body weight of rats treated with CFA of saline with no CFA treatment, saline after CFA treatment, IBU (ibuprofen) after CFA treatment, 1:2 IBU:90G prepared using acetone, and a IBU/lecithin oil containing 35% PC composition, PLx-2A-2.
Figure 14G:
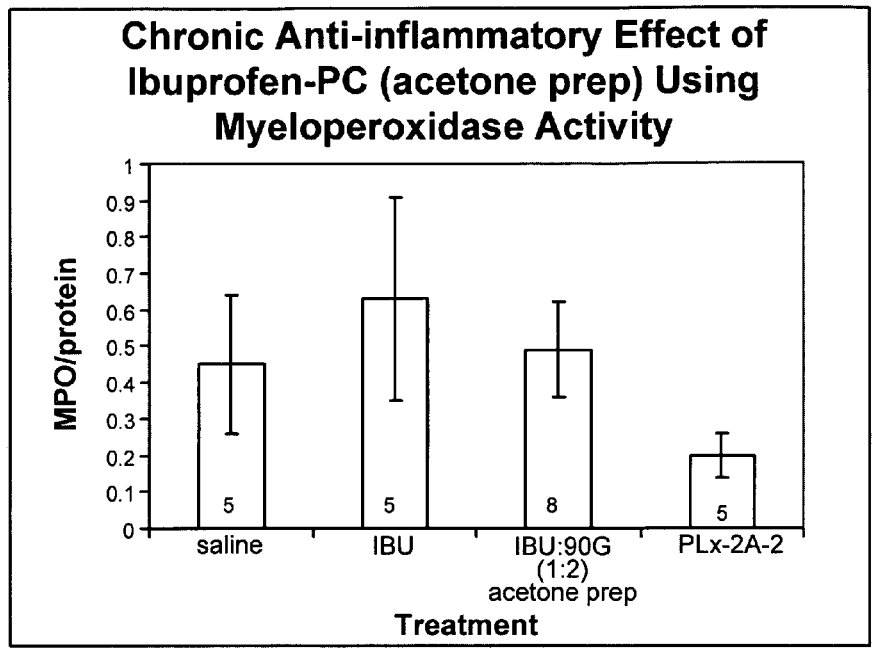
FIG. 14G depicts results of chronic anti-inflammatory effect as measured using myeloperoxidase in rats treated with CFA of saline with no CFA treatment, saline after CFA treatment, IBU (ibuprofen) after CFA treatment, 1:2 IBU:90G prepared using acetone, and a IBU/lecithin oil containing 35% PC composition, PLx-2A-2.

Looking at FIG. 14A, the anti-inflammatory effects are shown indicating that all three IBU formulations are equally efficacious. Looking at FIG. 14B, the hematocrit levels are shown indicating the 1:2 IBU:90G prepared using acetone formulation gave the best results of all the IBU formulations tested. Looking at FIG. 14C, the hemoglobin levels are shown indicating that the IBU:PC formulations are superior to IBU alone and showing the PLx-2A-2 material was prepared according to the procedures set forth in U.S. patent application Ser. No. 10/433,454, filed Nov. 6, 2003 was some what superior to the 1:2 IBU:90G prepared using acetone of this invention. Looking at FIG. 14D, the hemoglobin levels are shown indicating that the IBU:PC formulations are superior to IBU alone and that the 1:2 IBU:90G prepared using acetone was superior to the PLx-2A-2 material was prepared according to the procedures set forth in U.S. patent application Ser. No. 10/433,454 and similar to saline alone. Looking at FIG. 14E, the pain threshold results are shown indicating that the IBU:PC formulations are superior to IBU alone and showing the PLx-2A-2 material was prepared according to the procedures set forth in U.S. patent application Ser. No. 10/433,454, filed Nov. 6, 2003 was some what superior to the 1:2 IBU:90G prepared using acetone of this invention. Looking at FIG. 14F, body weight loss results are shown indicating that the IBU:PC formulations are superior to IBU alone and that the 1:2 IBU:90G prepared using acetone was superior to the PLx-2A-2 material was prepared according to the procedures set forth in U.S. patent application Ser. No. 10/433,454. Looking at FIG. 14G, the myeloperoxidase activity results are shown indicating that the IBU:PC formulations are superior to IBU alone and showing the PLx-2A-2 material was prepared according to the procedures set forth in U.S. patent application Ser. No. 10/433,454, filed Nov. 6, 2003 was some what superior to the 1:2 IBU:90G prepared using acetone of this invention.

Example 15

Figure 15A:
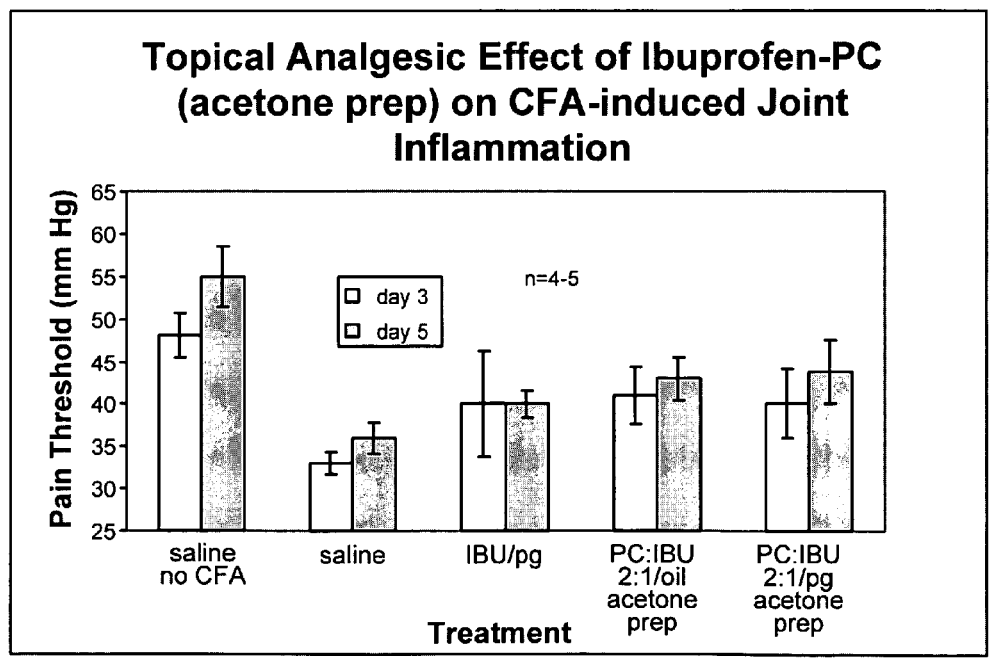
FIG. 15A depicts pain threshold results from topical analgesic effect on rats after CFA induced joint inflammation using saline with CFA treatment, saline after CFA treatment, ibuprofen in propylene glycol (IBU/pg), 2:1 ibuprofen:90G (PC:IBU 2:1/oil) oil prepared using acetone, and 2:1 ibuprofen:90G in propylene glycol (PC:IBU/pg) prepared using acetone.

Referring now to FIG. 15A, the effects of topically applied ibuprofen (IBU) formulations on rats after CFA induced joint inflammation were studied. The rats were treated with saline with no CFA treatment, saline after CFA treatment, ibuprofen in propylene glycol (IBU/pg) after CFA treatment, 2:1 ibuprofen:90G (PC:IBU 2:1/oil) oil prepared using acetone after CFA treatment, and 2:1 ibuprofen:90G oil in propylene glycol (PC:IBU/pg) prepared using acetone after CFA treatment. Again, the study was carried out in accordance with the experimental description given above.

Figure 15B:
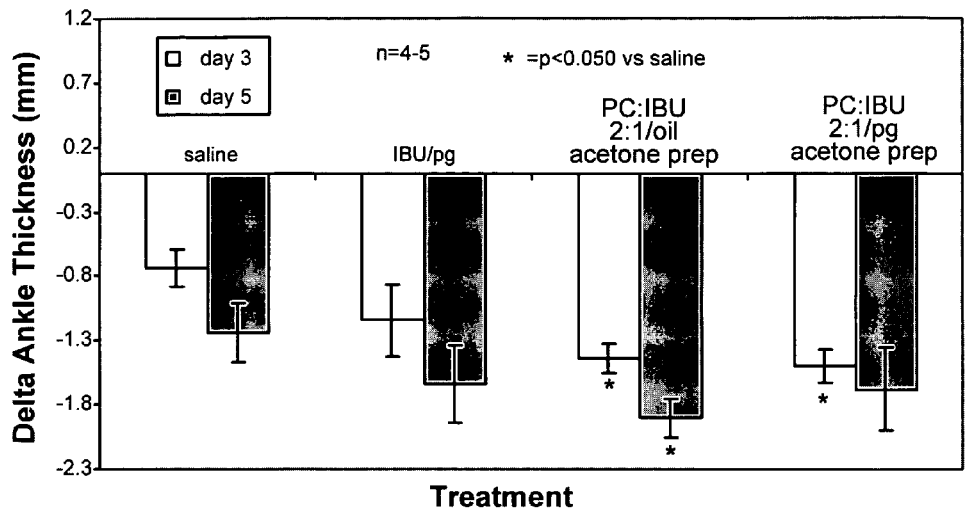
FIG. 15B depicts delta ankle thickness results from topical anti-inflammatory effect on rats after CFA induced joint inflammation using saline with CFA treatment, saline after CFA treatment, ibuprofen in propylene glycol (IBU/pg), 2:1 ibuprofen:90G (PC:IBU 2:1/oil) oil prepared using acetone, and 2:1 ibuprofen:90G in propylene glycol (PC:IBU/pg) prepared using acetone.
Figure 15C:
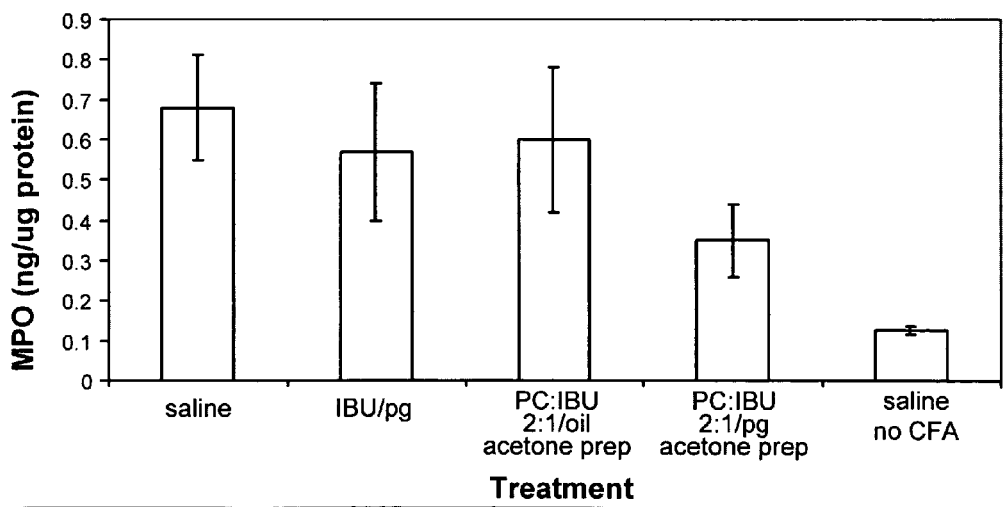
FIG. 15C depicts myeloperoxidase (MPO) activity results from topical anti-inflammatory effect on rats after CFA induced joint inflammation using saline with CFA treatment, saline after CFA treatment, ibuprofen in propylene glycol (IBU/pg), 2:1 ibuprofen:90G (PC:IBU 2:1/oil) oil prepared using acetone, and 2:1 ibuprofen:90G in propylene glycol (PC:IBU/pg) prepared using acetone.

Looking at FIG. 15A, pain threshold results are shown indicating that all IBU formulations were superior to saline and that the IBU:PC formulations were similar to IBU at three day out, but superior to IBU at five days out. Looking at FIG. 15B, delta ankle thickness results are shown indicating that all IBU formulations decreases ankle inflammation compared to saline and that both IBU:PC formulations were superior to IBU alone in both three and five day tests. Looking at FIG. 15C, myeloperoxidase (MPO) activity results are shown indicating similar behavior with the IBU formulations with 2:1 ibuprofen:90G in propylene glycol (PC:IBU/pg) prepared using acetone showing the lowest MPO activity.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

I claim:

1. A method of preparing a phospholipid-non-steroidal anti-inflammatory drug composition comprising purified phospholipid-non-steroidal anti-inflammatory drug associated complexes comprising the steps of:

contacting a selective or nonselective non-steroidal anti-inflammatory drug (sns-NSAID) with an amount of phospholipid (PL) at a temperature between 40° C. and 60° C. in a polar solvent to produce a solution including the PL-sns-NSAID associated complexes, where the amount of the PL is in excess of an amount of the PL normally soluble in the solvent in the absence of the sns-NSAID and where the amount of the excess PL is below an amount based on the amount of sns-NSAID where the PL begins to precipitate out of the solution; and substantially removing the polar solvent by evaporation to form a phospholipid-non-steroidal anti-inflammatory drug associated composition comprising purified PL-sns-NSAID associated complexes in the form of a homogenous oil; wherein a weight ratio of sns-NSAID to PL in the purified phospholipid-non-steroidal anti-inflammatory drug associated composition is between 1:2 and 1:4;

wherein the sns-NSAID is selected from the group consisting of ibuprofen, aspirin, salicylic acid, naproxen, indomethacin, diclofenac, fluobiprofen flurbiprofen, ketoprofen and mixtures or combinations thereof; and wherein the polar solvent is acetone.

2. The method of claim 1, wherein the phospholipid is one or more compounds of the general formula:

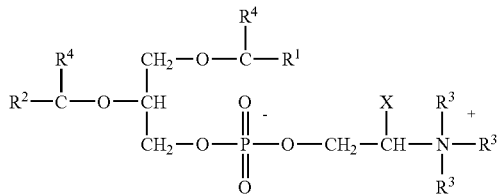

where $R^1$ and $R^2$ are saturated or unsaturated substitutions ranging from 8 to 32 carbon atoms; $R^3$ is H or $CH_3$, and X is H or COOH; and $R^4$ is =O or $H_2$.

3. The method of claim 1 wherein the phospholipid is selected from the group consisting of phosphatidylcholine (PC), dipaimitoylphosphatidylcholine (DPPC), other disaturated phosphatidylcholines, phosphatidylethanolamines, phosphatidylinositol, phosphatidyl serines sphingomyelin or other ceramides, lecithin oils derived from soy beans, dimyristoyl phosphatidylcholine, distearoylphosphatidylcholine, dilinoleoyiphosphatidylcholine (DLL-PC), soy phophatidylchioine (Soy-PC or PCs), egg phosphatidycholine (Egg-PC or PC), and mixtures or combinations thereof.

4. The method of claim 1, further comprising:

prior to the removing step, cooling the solution for a cooling time and at a cooling temperature, where the cooling time and cooling temperature are sufficient to precipitate any PL not associated with the sns-NSAID or any PL in excess of an associated amount;

if a precipitate forms, centrifuging the cooled solution to form a precipitate and a supernatant; and separating the precipitate from the supernatant.

* * * * *